United States Patent
Kwon et al.

(10) Patent No.: US 6,340,770 B1
(45) Date of Patent: Jan. 22, 2002

(54) PLATINUM (IV) COMPLEX USED AS ANTI-CANCER AGENT AND PREPARING METHOD THEREOF

(75) Inventors: Young-Ee Kwon; Kyu Ja Whang; Won Kyu Kim, all of Seoul (KR)

(73) Assignees: Sook Myung Women's University; STC Nara Co., Ltd., both of Seoul (KR)

( * ) Notice: Subject to any disclaimer, the term of this patent is extended or adjusted under 35 U.S.C. 154(b) by 0 days.

(21) Appl. No.: 09/474,129

(22) Filed: Dec. 29, 1999

(30) Foreign Application Priority Data

May 20, 1999 (KR) .......................... 99-16801

(51) Int. Cl.⁷ .................... C07F 15/00; A61K 31/28
(52) U.S. Cl. ........................ 556/137; 514/492
(58) Field of Search ................. 556/137; 514/492

(56) References Cited

U.S. PATENT DOCUMENTS

| | | | | |
|---|---|---|---|---|
| 5,288,887 A | * | 2/1994 | Khokhar et al. ............ | 556/137 |
| 5,902,826 A | * | 5/1999 | Mogi et al. ................. | 514/492 |

* cited by examiner

*Primary Examiner*—Porfirio Nazario-Gonzalez

(57) ABSTRACT

The present invention is related to a novel Pt(IV) complex represented by the following Chemical Formula 3 used as an anti-cancer agent and preparation method thereof.

<Chemical Formula 3>

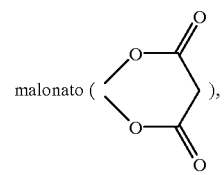

wherein,

X is $Cl_2$, malonato ( 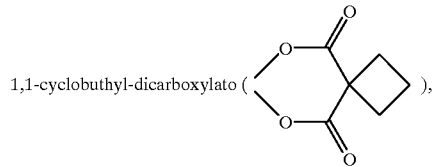 ), 1,1-cyclobuthyl-dicarboxylato (  ), oxalato ( 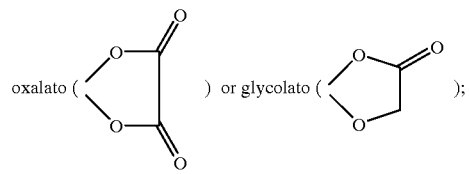 ) or glycolato (  );

and $R_1$ and $R_2$ are independently —OH, —Cl, —OCOCH$_3$, —OCOCF$_3$, —OCO(CH$_2$)$_n$CH$_3$ or —OCO(CH$_2$)$_n$CF$_3$ (n is an integer of 1 to 4).

15 Claims, 17 Drawing Sheets

6hr pass after ip injection

1day pass after ip injection

3day pass after ip injection

7day pass after ip injection

6hr pass after ip injection

1day pass after ip injection

3day pass after ip injection

7day pass after ip injection

6hr pass after ip injection

1day pass after ip injection

3day pass after ip injection

7day pass after ip injection

PLATINUM (IV) COMPLEX USED AS ANTI-CANCER AGENT AND PREPARING METHOD THEREOF

BACKGROUND OF THE INVENTION

1. Field of the Invention

The present invention is related to a novel Pt(IV) complex used as an anti-cancer agent and preparing method thereof and more particularly a novel Pt(IV) complex having an octahedral structure and preparing method thereof.

2. Description of the Prior Art

Nowadays, many people suffer from cancer, and it is one of the most painful diseases. Since discovering a cancer, humans have constantly taken various efforts in researching in order to overcome the cancer, such as development of an anti-cancer agent, genetic treatment, operative treatment, radiotherapeutics and so on.

For example, platinum complexes, such as cis-Diaminedichloroplatinum(II) (hereinafter, referred to as cisplatin) which is known as an effective anti-cancer agent, are widely used in a clinical field, and its various derivatives are under a clinical trial or under development. Among them, cisplatin[1-2], first disclosed in 1972, shows an excellent treatment effect in ovarian cancer, urinary bladder cancer and particularly prostatic cancer which is difficult to be treated using conventional anti-cancer agents. [3-10]

As shown in the following Chemical Formula I, cisplatin is a Pt(II) complex wherein Pt in center is stably combined with amines.

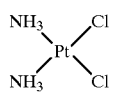

<Chemical Formula 1>

As same as conventional alkylating agent, anti-cancer mechanism of cisplatin is caused by position-exchanging between chlorine coordinate and DNA for forming a stable bonding state[66-67], and therefore DNA structure comes to be significantly changed. [68-69]

When dispensing cisplatin into especially where chlorine concentration is high (103 mM), such as blood, lymph and intestinal fluid, dissociation of chlorine ion from cisplatin is repressed because of high concentration of chlorine, and cisplatin comes to be permeated into cell by passive diffusion in the form of non-charged complex and subject to hydrolysis to be diaqua complex. It was reported that such phenomenon was because the chlorine concentration in cell was lower by thirty-folds than that of outside cell.[91] Once permeated into cell, positively-ionized cisplatin in the form of aqua-complex, such as $Pt(OH)_2(NH_3)_2$ and $Pt(OH)(OH_2)(NH_3)_2$, binds to DNA helix by electrical attraction.[92-93]

The rate of binding between cisplatin and DNA is same in both cancer cell and normal cell. However, comparing with normal cell, the growth rate of cancel cell is very fast and repairing rate is very slow when it is damaged. Therefore, hindrance caused by cisplatin is more significant in cancer cell than normal cell.

However, the clinical use of cisplatin has been frequently limited by the following drawbacks:

(1) Serious toxicity, such as nephrotoxicity, gastrointestinal toxicity, ototoxicity and neurotoxicity.[15-17] Particularly, nephrotoxicity is very serious. Nephrotoxicity by cisplatin is mainly due to dose-limiting[22], that is, toxicity becomes serious as dose increases, which gives a rise to tubulorrhexis. Thereby, toxicity is directly manifested into renal cortex, and distal renal tubule, collecting tubule and particularly renal proximal tubule become damaged;[23-26]

(2) Low activity for certain kinds of cancers, such as breast and colon cancers;[18]

(3) Development of acquired resistance;[19-21] and (4) Poor solubility in water.

In an attempt to overcome these drawbacks of cisplatin, the $2^{nd}$-generation Pt complex, cis-diamine(1,1-cyclobutanedicarboxylato)platinum(II) (hereinafter, referred to carboplatin) was developed and is commercially available at present.

Carboplatin (Chemical Formula II), a compound where chlorine group of cisplatin is substituted with 1,1-cyclobutanedicarboxylato, is regarded as a good anti-cancer agent in that it shows lesser side effects such as nephrotoxicity and nausea if compared with cisplatin[31-32]. Also, it has a sufficient solubility and shows similar effectiveness to cisplatin against ovarian cancer and small cell carcinoma in lung.[33-34]

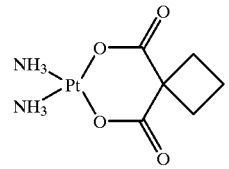

<Chemical Formula II>

However, Carboplatin also has a narrow anti-cancer spectrum[33],[35] and it is not effective in the treatment of cancer cells resistant to cisplatin, suggesting that cross-resistance between cisplatin and carboplatin.[36-37]

The resistance-existent mechanism against cisplatin is as follows:

First, when Pt complex attacks DNA, the repairing rate of a damaged DNA increases and a low-molecular weight of cell compound, such as glutathion having thiol group, increases. Thus, the agent is inactivated, and re-absorption of the agent into cell comes to be decreased.

Accordingly, anti-cancer agent in the future must be able to inhibit resistant cells. It is because that cancer cell comes to have resistance against cisplatin which has been used as anti-cancer agent during about 30 years. At present, even though various Pt(II) complexes is under development and experimentation, any one has limits and some problems. Thus, its substitutes are required.

In addition, in order to alleviate the pain of cancer patients, development of Pt complex capable of being used not only as injection but also as oral administration is required. As a compound capable of meeting such a requirement, at present, Pt(IV) complexes are considered.

Besides, there are many requirements which a new anti-cancer agent should meet, such as good water-solubility and lipophilicity, a low risk of nephrotoxicity and so on.

Figure 14:
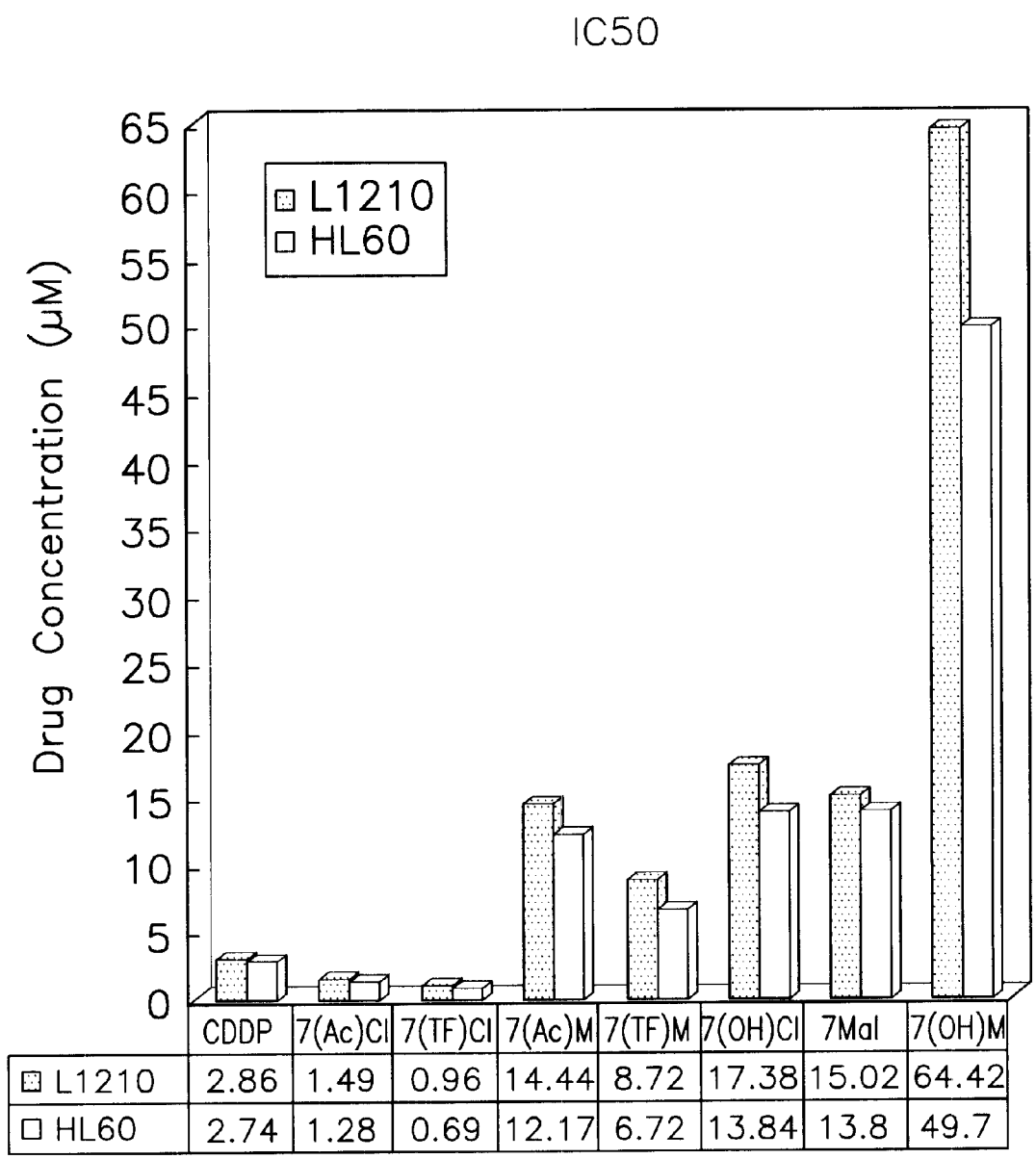

The FIG. 14 is a bar graph comperatively showing $IC_{50}$ of novel Pt(IV) complexes according to the present invention and a conventional cisplatin.

SUMMARY OF THE INVENTION

The object of the present invention is to provide a novel anti-cancer agent, and preparing method thereof, which (i) has an excellent anti-cancer ability; (ii) shows an effectiveness to resistant cell of cisplatin; (iii) has good lipophilicity and low nephrotoxicity; and (iv) is capable of using for oral administration.

Another abject of the present invention is to provide a pharmaceutical composition used as an anti-cancer agent.

In order to achieve the object of the present invention, Pt(IV) complex represented by the following Chemical Formula 3 is provided.

<Chemical Formula 3>

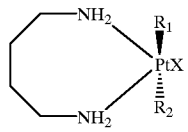

wherein,

X is $Cl_2$,

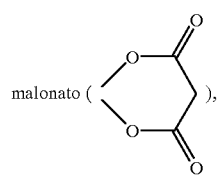

malonato ( ),

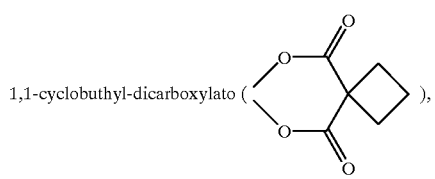

1,1-cyclobuthyl-dicarboxylato ( ),

-continued

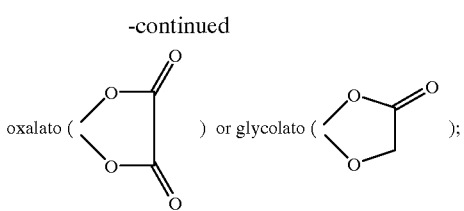

oxalato ( ) or glycolato ( );

$R_1$ and $R_2$ are independently —OH, —Cl, —OCOCH$_3$, —OCOCF$_3$, —OCO(CH$_2$)$_n$CH$_3$ or —OCO(CH$_2$)$_n$CF$_3$; and n is an integer among 1 to 4.

In order to achieve the second object of the present invention, it is provided a pharmaceutical composition containing (i) a compound represented by the above Chemical Formula 3 as an effective component and (ii) a pharmaceutically acceptable carrier.

DETAILED DESCRIPTION OF THE PRESENT INVENTION

After many researches and experiments, we, inventors, discovered that the following Pt (IV) complex represented by the Chemical Formula 3 has excellent characteristics as an anti-cancer agent.

<Chemical Formula 3>

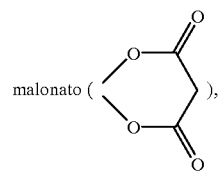

wherein,

X is $Cl_2$,

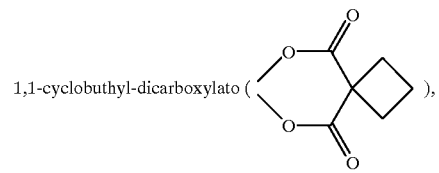

malonato ( ), 1,1-cyclobuthyl-dicarboxylato ( ),

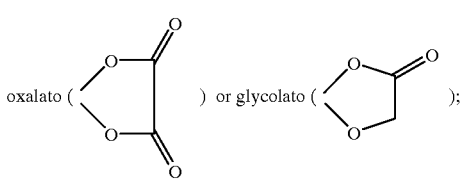

oxalato ( ) or glycolato ( );

$R_1$ and $R_2$ are independently —OH, —Cl, —OCOCH$_3$, —OCOCF$_3$, —OCO(CH$_2$)$_n$CH$_3$ or —OCO(CH$_2$)$_n$CF$_3$; and n is an integer among 1 to 4.

The compound represented by the Chemical Formula 3 is 7-membered ring Pt complex, thus showing a better anti-cancer activity than cisplatin.

The coordinates consisting the 7-membered ring are 1,4-butanediamines. The reason of not introducing an additional functional group into the 1,4-butanediamine is because the ring size of 7-membered ring itself is larger than 5-membered ring or 6-membered ring, thus making the DNA helix structure be seriously distorted when the 7-membered ring binds to DNA. That is, if an additional functional group is introduced, the size of the molecule becomes larger and thus the possibility of causing toxicity due to transformation of DNA structure becomes high.

As a leaving ligand, chlorine coordinate having good lipophilicity or malonate which is bio-metabolite having good water-solubility can be introduced.

In addition, in order to overcome the anti-cancer activity limit of Pt(II) complex having a plane structure and improve the bioavailability, axial groups are introduced, thus having an octahedral structure.

Pt (IV) complex, which is generally obtained by oxidation of Pt(II) complex, increase liphopilicity in vivo and thus enhances bioavailability. Furthermore, it is reported that Pt(IV) show low toxicity because it acts in the form of prodrug. That is, it is first reduced into Pt(II) in vivo and then activated as an anti-cancer agent.

As more preferred compound according to the present invention, there are compounds represented by the following Chemical Formulas 4 to 9.

(1) trans, cis-dihydroxo,dichloro-1,4-butanediamine Pt(IV) complex (hereinafter, referred to be 7(OH)Cl)

<Chemical Formula 4>

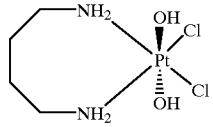

As shown in the following Reaction Equation 1, the Pt(IV) complex represented by the above formula 4 is obtained by adding 30% $H_2O_2$ into dichloro-1,4-butanediamine Pt(II) complex to oxidize the Pt(II) complex of a plane structure. Thereby, hydroxy group is introduced in axial positions and the octahedral structure is obtained. Here, dichloro-1,4-butanediamine Pt(II) complex may be obtained by conventional method as shown in the following Reaction Equation 1.

Reaction Equation 1

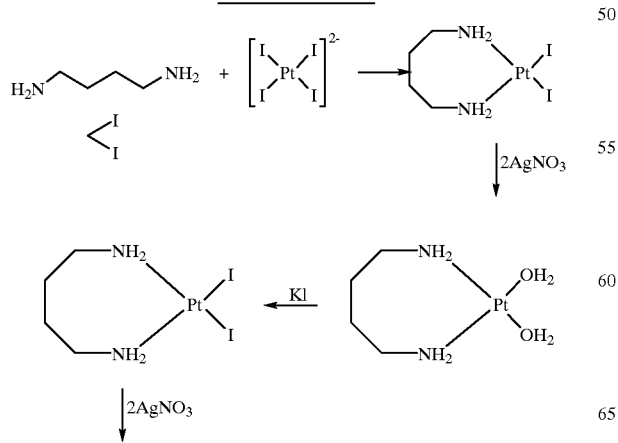

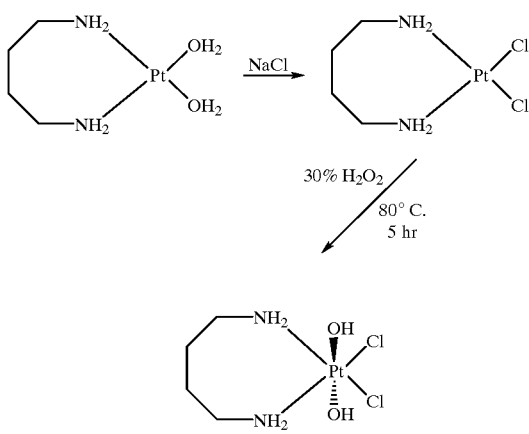

(2) trans, cis-diacetato,dichloro-1,4-butanediamine Pt(IV) complex (hereinafter, referred to be [7(Ac)Cl])

<Chemical Formula 5>

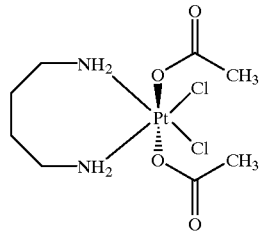

The Pt (IV) complex represented by the Chemical Formula 5 is obtained by introducing acetyl group into the compound represented by the Chemical Formula 4 i.e., 7(OH)Cl, which is performed by adding an in excessive amount of acetic anhydride to 7(OH)Cl in $CH_2Cl_2$ solvent for polymerization as shown in the following Reaction Equation 2.

Reaction Equation 2

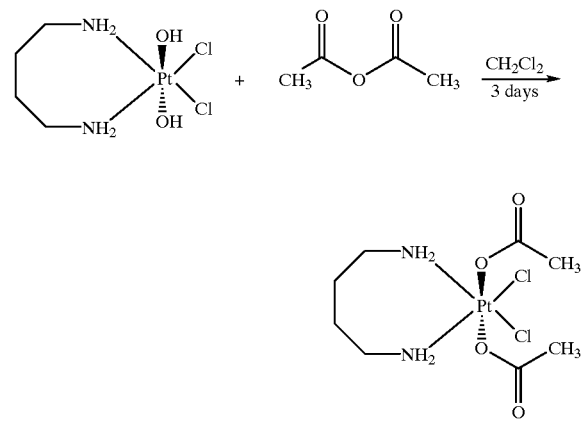

(3) trans, cis-ditriflioroacetato,dichloro-1,4-butanediamine Pt(IV) complex (hereinafter, referred to be [7(TF)Cl])

<Chemical Formula 6>

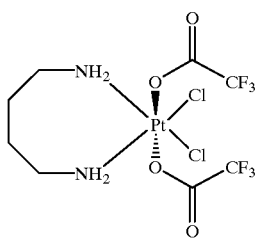

The Pt (IV) complex represented by the above Chemical Formula 6 is obtained by adding an excessive amount of trifluoracetic anhydride to 7(OH)Cl as shown in the following Reaction Equation 3.

Reaction Equation 3

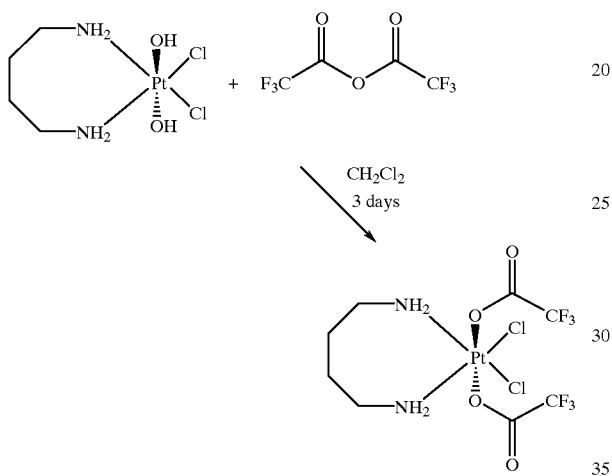

(4) trans-dihydroxo,malonato-1,4-butanediamine Pt(IV) complex (hereinafter, referred to be [7(OH)M])

<Chemical Formula 7>

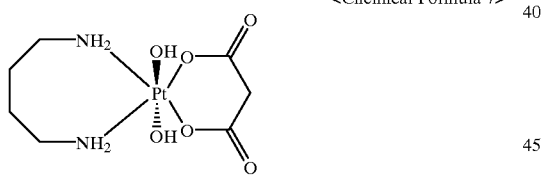

The Pt(IV) complex represented by the Chemical Formula 7 is obtained as shown in the following Reaction Equation 4.

First, cis-diiodo-1,4-butanediamine Pt(II) complex and disilver malonate salt are reacted. Then, after removing precipitate AgI, the resultant solution is concentrated to obtain malonato-1,4-butanediamine Pt(II) complex (hereinafter, referred to be 7M) in the type of imbricate precipitate.

Then, an excessive amount of 30% $H_2O_2$ is added to the 7M to generate [7(OH)M].

Reaction Equation 4

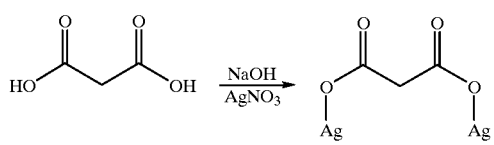

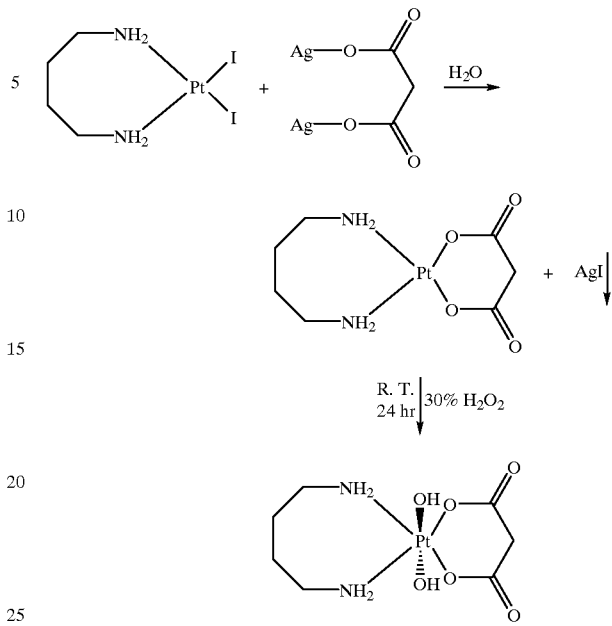

(5) trans-diacetato,malonato-1,4-butanediamine Pt (IV) complex (hereinafter, referred to be [7(Ac)M])

<Chemical Formula 8>

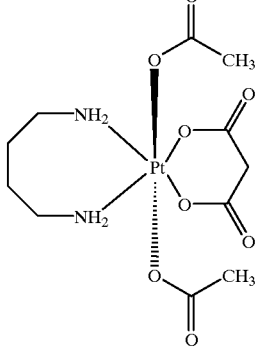

The Pt(IV) represented by the Chemical Formula 8 is obtained as shown in the following Reaction Equation 5. That is, an excessive amount of acetic anhydride is added to 7(OH)M in $CH_2Cl_2$ solvent. Then, the resultant solution is subject to re-crystallization using a solvent prepared by mixing water and methanol in the ratio of 3:2 respectively, to obtain [7(Ac)M] in the type of white acicular crystal.

Reaction Equation 5

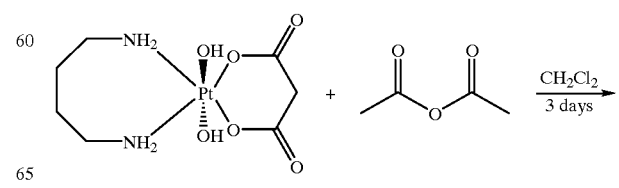

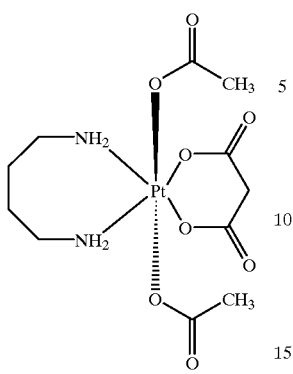

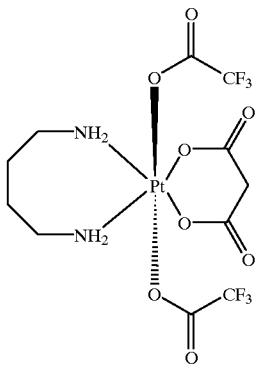

(6) trans-ditrifluoroacetato,malonato-1,4-butanediamine Pt(IV) complex (hereinafter, referred to be [7(TF)M])

<Chemical Formula 9>

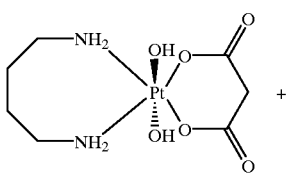

The Pt (IV) complex represented by the Chemical Formula 9 contains fluoro atoms enabling to enhance bioavailability and can be obtained as shown in the following Reaction Equation 6.

That is, first, trans-trifluoroacetato,malonato-1,4-butanediamine Pt(IV) complex (hereinafter, referred to be [7(TF)M]) is obtained by adding an excessive amount of trifluoroacetic anhydride to 7(OH)M, the [7(TF)M] is purified using methanol to be transparent cube type.

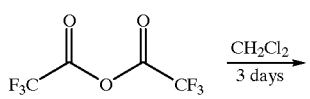

Synthesis and Structure Examination

Hereinafter, preferable synthesis of Pt (IV) complex according to the present invention and the structure of compound obtained thereby will be described.

EXAMPLE 1

Synthesis of trans,cis-dihydroxo,dichloro-1,4-butanediamine Pt(IV) complex [7(OH)Cl]

30% $H_2O_2$ (30 ml) was added to 3 g of [7Cl] (8.48 mM) in water (100 ml) and then reaction was performed at 80° C. for 5 hours. After completion of the reaction, the solution was depressively concentrated to generate white-yellow precipitate. After adding 300 ml of methanol into the precipitate, the resultant is disposed at 4° C. over 2 hours. Then, the resultant was filtered, washed using methanol and dried at 60° C. under depression to generate 2.17 g of white-yellow precipitate Yield: 65.95%

IR (KBr,cm$^{-1}$): 3502, 3200, 1572, 1027, 545

$^1$H-NMR (D$_2$O): 3.2(2H), 2.8(4H), 2.5(4H), 1.7(4H),

Elemental analysis:

Calc. for $C_4H_{14}N_2Cl_2O_2Pt$

C; 12.37%, H; 3.61%, N; 7.22%, O; 8.25%

Found for C; 12.35%, H; 3.63%, N; 7.25%, O; 8.25%

In order to confirm OH group of the obtained [7(OH)Cl], IR spectroscopic analysis was performed. As a result, strong vibration of O—H bond was shown as a single peak around 3500 cm$^{-1}$ and vibration of N—H bond was appeared widely around 3200 cm$^{-1}$.

EXAMPLE 2

Synthesis of trans,cis-diacetato,dichloro-1,4-butanediamine Pt(IV) complex: [7(Ac)Cl]

20 ml of acetic anhydride was added to 1 g of 7(OH)Cl (2.577 mM) in 100 ml of methylenechloride, and then the resultant solution was subject to reflux for 3 days. Then, the resultant was subject to depressively concentration to generate precipitates. After dissolving the precipitates in methanol, the resultant solution was filtered and the filterated solution was re-crystalized to generate transparent light-yellow cube type of precipitate (0.96 g).

| | |
|---|---|
| Yield | 78.9% |
| IR(KBr,cm$^{-1}$) | 3159, 3039, 1598, 1363, 1295, 986, 704, 503 |
| $^1$H-NMR(DMSO-d$_6$) | 7.9(4H), 2.5–2.7(4H), 1.9–2.0(6H), 1.65(4H) |
| $^1$H-NMR(CD$_3$OD) | 2.85–2.95(4H), 2.1(6H), 1.85(4H) |

-continued

| $^{13}$C-NMR(CD$_3$OD) | 183.1, 49.5, 49.3, 49.1, 49, 48.8, 48.6, 48.5, 48.2, 27.6, 23.6 |
|---|---|

Elemental analysis:

Calc. for $C_8H_{18}N_2Cl_2O_4Pt$:
C; 20.34%, H; 3.81%, N; 5.93%,

Found for C; 20.33%, H; 3.80%, N; 5.93%,

The structure of the obtained compound in form of precipitate was confirmed by IR, NMR, Elemental analysis and X-ray diffraction.

As a result of IR, strong vibration peak by O—H bond was observed around 3500 cm$^{-1}$.

According to $^1$H-NMR using DMSO-d$_6$ as solvent, a peak by N—H bond was observed between 7.8 around 7.9 ppm, and peaks by hydrogen consisting of alkyl group were observed between 1.6 and 3.9 ppm.

Referring to the result of the examination, four H peaks bonded to 2 carbons farthest from amine were observed at 1.85 ppm, six H peaks of two methyl groups on axial ligands were at 2.1 ppm, and four H peaks of two methyl groups next to the amine were at 2.9 ppm.

According to $^{13}$C-NMR, a C peak of carbonyl group was observed at 183.1 ppm.

In addition, as shown in the above Elemental analysis, the experimental value of content ratio of carbon, hydrogen and nitrogen consisting of a molecule was identical to the calculated value.

Figure 1:
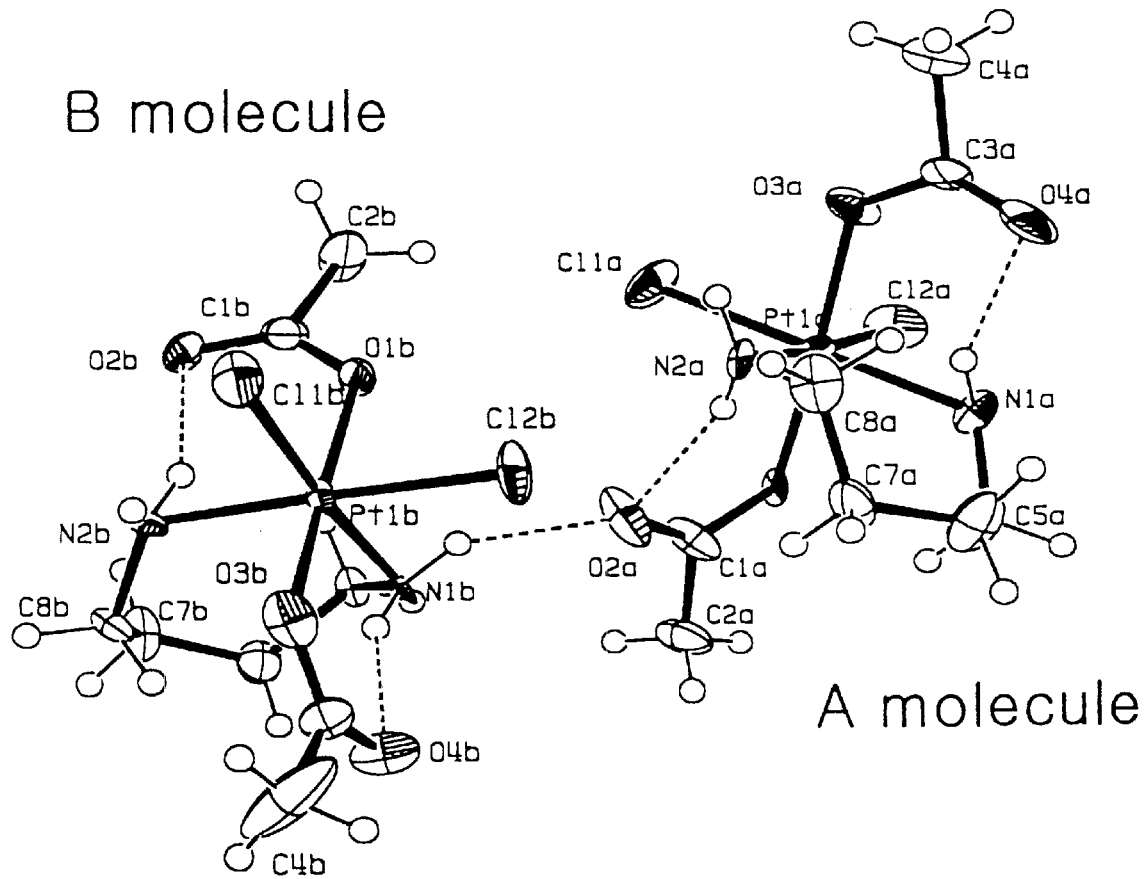
FIGS. 1 to 3 show crystal structures of Pt(IV) complexes according to the present invention, which are detected by X-ray diffraction method, respectively.

FIG. 1. shows a molecule structure of [7(Ac)Cl] synthesized in Example 2, which is obtained by X-ray diffraction method. As shown in FIG. 1, 7(Ac)Cl consists of 2 molecules (A, B) each of which has a similar conformation and is bonded to each other by hydrogen bond in the form of N(1B)—H . . . O(2A). In A molecule, the hydrogen bonds are between N(1a)—H and O(4a), and between N(2a)—H and O(2a). Also, in B molecule, the hydrogen bonds are in the same positions as A molecule. In addition, the 7-membered ring structure consisted of Pt(IV) ion and 1,4-butanediamine and has twist-chair type of conformation.

The following Table 1 which is obtained by X-ray diffraction shows bond length and bond angle between Pt and neighboring elements in [7(Ac)Cl] complex.

TABLE 1

Bond Length and Angle of trans,cis-Diacetato, dichloro-(1,4-butanediamine) Pt(IV) complex

|  | A | B |
|---|---|---|
| Pt(1)-O(1) | 2.013(12)Å | 2.014(14)Å |
| Pt(1)-O(3) | 1.998(14)Å | 2.018(15)Å |
| Pt(1)-N(1) | 2.058(16)Å | 2.052(15)Å |
| Pt(1)-N(2) | 2.055(14)Å | 2.054(16)Å |
| Pt(1)-Cl(1) | 2.302(5)Å | 2.304(5)Å |
| Pt(1)-Cl(2) | 2.315(5)Å | 2.302(5)Å |
| O(3)-Pt(1)-O(1) | 175.6(6) | 176.1(6) |
| O(3)-Pt(1)-N(2) | 85.4(7) | 84.5(6) |
| O(1)-Pt(1)-N(2) | 96.5(6) | 98.7(6) |
| O(3)-Pt(1)-N(1) | 97.6(7) | 97.2(6) |
| O(1)-Pt(1)-N(1) | 86.2(6) | 84.5(6) |
| N(2)-Pt(1)-N(1) | 98.0(6) | 98.6(6) |
| O(3)-Pt(1)-Cl(1) | 83.6(5) | 86.1(5) |
| O(1)-Pt(1)-Cl(1) | 92.5(4) | 91.9(4) |
| N(2)-Pt(1)-Cl(1) | 85.7(5) | 84.9(4) |
| N(1)-Pt(1)-Cl(1) | 176.3(5) | 175.3(4) |
| O(3)-Pt(1)-Cl(2) | 90.3(5) | 90.2(5) |
| O(1)-Pt(1)-Cl(2) | 87.7(4) | 86.5(4) |
| N(2)-Pt(1)-Cl(2) | 175.2(5) | 174.0(5) |
| N(1)-Pt(1)-Cl(2) | 84.6(5) | 84.9(4) |
| Cl(1)-Pt(1)-Cl(2) | 91.9(2) | 91.8(2) |

Wherein the above X-ray diffraction anlaysis, reliability R was 0.071.

EXAMPLE 3

Synthesis of trans,cis-Trifluoroacetato,dichloro-1,4-butanediamine Pt(IV) complex-[7(TF)Cl]

Trifluoroacetic anhydride (15 ml) was added to 1 g (2.577 mM) of 7(OH)Cl in 100 ml of methylene chloride and the resultant solution was subject to reaction for 3 days with reflux. Then, the resultant solution was subject to repressive-concentration to generate precipitate. The precipitate was dissolved into methanol, filtered and re-crystalized to obtain transparent light-yellow diamond-type of crystal (1.22 g).

| Yield | 81.62% |
|---|---|
| IR(KBr,cm$^1$) | 3254, 3209, 3177, 1724, 1565, 1376, 1166, 739 |
| $^1$H-NMR(DMSO-d$_6$) | 7.4(4H), 2.5–2.75(4H), 1.7(4H) |
| $^1$H-NMR(CD$_3$OD) | 3.0—2.8(4H), 1.85(4H) |
| $^{13}$C-NMR(CD$_3$OD) | 165.4, 165.1, 115, 112.7, 49.5, 49.3, 49,48.8, 48.5, 47.8, 26.9 |

Elemental analysis:

Calc. for $C_8H_{12}N_2Cl_2O_4F_6Pt$
C; 16.55%, H; 2.07%, N; 4.83%,

Found for C; 16.54%, H; 2.08%, N; 4.80%,

The structure of the obtained compound in light yellow hexagonal crystal was confirmed by IR, NMR, Elemental analysis and X-ray diffraction.

IR showed no peaks around 3500 cm$^{-1}$ due to disappearance of O—H bond and showed one peak around 1700 cm$^{-1}$ due to carbonyl (C=O) bond. While the general vibration peak by carbonyl bond appears at 1600 cm$^{-1}$, it is assumed that the carbonyl peak in [7(TF)Cl] appears at lower wave-length by about 100 cm$^{-1}$ is because fluorine atom having a strong electron affinity attracts the electrons in neighboring carbonyl group, and therefore the carbonyl group lacks the electrons.

Referring to the result of $^1$H-NMR ananlysis using DMSO-d$_6$ solvent, a H peak of amine was observed at 7.4 ppm, which moved by about 0.5 ppm in the direction of high magnetic field if compared with Pt complex containing acetyl group. It appears to be caused by electron affinity of the fluorine atom.

A H peak of alkyl group appeared between 1.7–2.8 ppm. However, since the peak was not clear, re-experiment was performed using CD$_3$OD solvent. As a result, four H peaks bonded to two carbons farthest from amine were observed at 1.85 ppm, and four H peaks of two methyl groups next to the amine were observed at 2.9 ppm.

Referring to $^{13}$C-NMR spectra, two carbon peaks of carbonyl groups were observed at 165.1 ppm and 165.4 ppm respectively which is moved by about 18 ppm in the direction of high magnetic field, comparing with 7(Ac)Cl of which the carbonyl peak was appeared at 183.1 ppm. It seems that fluorine atom is the cause. The carbon peaks of alkyl group were appeared between 47.8–49.5 ppm.

In addition, the content ratio of carbon, hydrogen and nitrogen consisting of the molecule detected by experiment was substantially identical to the calculated value.

Figure 2:
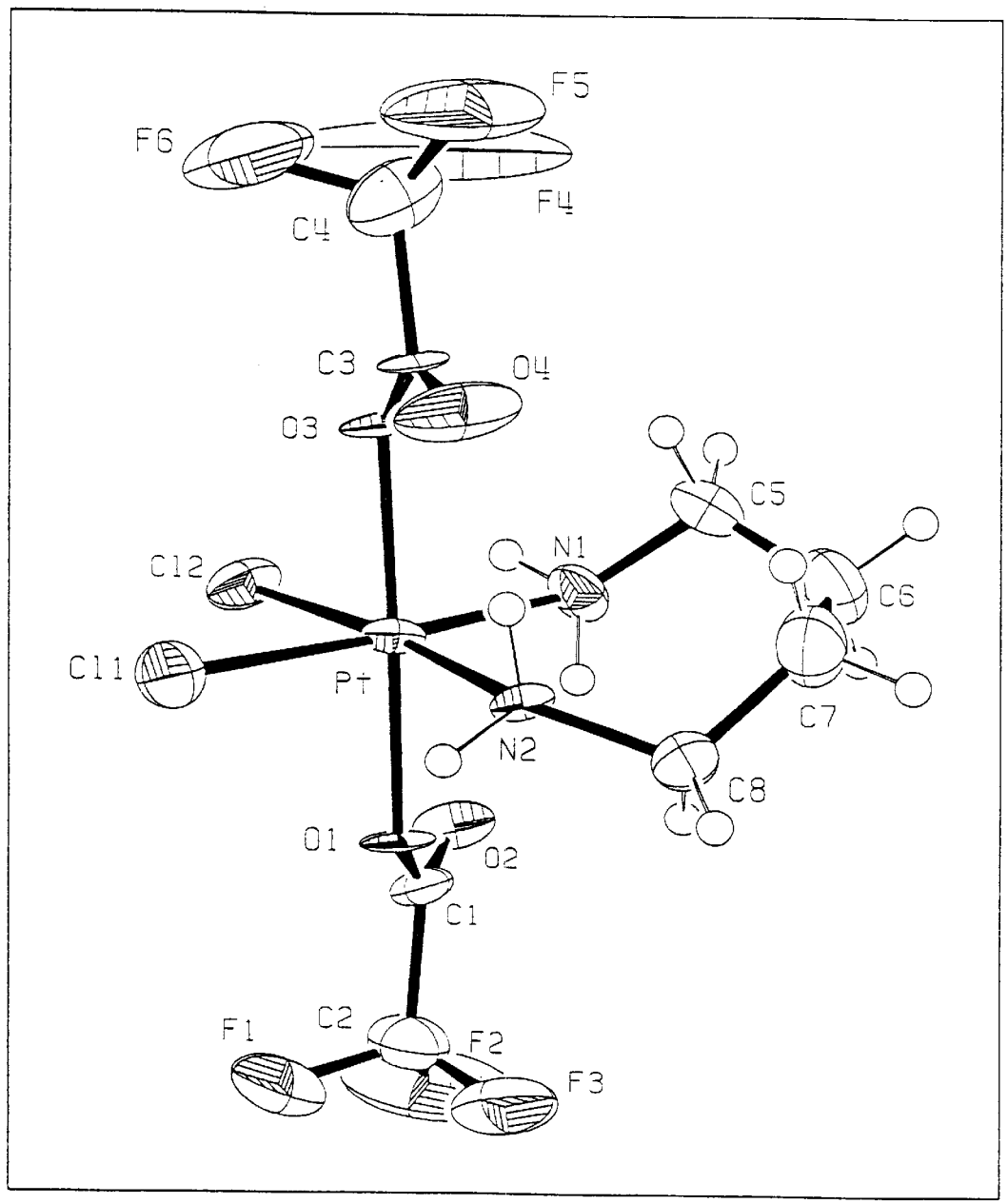

In order to examine the molecular structure of the synthesized [7(TF)Cl], its X-ray crystal structure was detected using X-ray diffraction method and the result is shown in FIG. 2.

As shown in FIG. 2, [7(TF)Cl] has also hydrogen bonds which are between N2—H and O4, and between N1—H and O2, respectively. In addition, as same as 7(Ac)Cl, the 7-membered ring consisted of Pt ion and 1,4-butanediamine was twist-chair form.

The following Table 2 shows bond lengths and bond angles between Pt and its neighboring elements, which is detected by X-ray crystal structure.

TABLE 2

Bond Length and Angle of trans,cis-ditrifluoroacetato, dichloro-(1,4-butanediamine)Pt(IV) complex

| | |
|---|---|
| Pt-O(1) | 2.002(7) |
| Pt-O(3) | 2.015(7) |
| Pt-N(2) | 2.040(9) |
| Pt-N(1) | 2.080(9) |
| Pt-Cl(1) | 2.303(3) |
| Pt-Cl(2) | 2.306(3) |
| O(1)-Pt-O(3) | 178.5(3) |
| O(1)-Pt-N(2) | 82.5(4) |
| O(3)-Pt-N(2) | 98.5(4) |
| O(1)-Pt-N(1) | 94.0(4) |
| O(3)-Pt-N(1) | 87.1(4) |
| N(2)-Pt-N(1) | 95.5(4) |
| O(1)-Pt-Cl(1) | 88.7(2) |
| O(3)-Pt-Cl(1) | 90.2(2) |
| N(2)-Pt-Cl(1) | 86.0(3) |
| N(1)-Pt-Cl(1) | 177.1(3) |
| O(1)-Pt-Cl(2) | 93.6(2) |
| O(3)-Pt-Cl(2) | 85.3(2) |
| N(2)-Pt-Cl(2) | 174.3(3) |
| N(1)-Pt-Cl(2) | 88.9(3) |
| Cl(1)-Pt-Cl(2) | 89.8(9) |

Wherein, reliability (R) of X-ray diffraction analysis was 0.035.

EXAMPLE 4

Synthesis of trans-Hydroxy,malonato-1,4-butanediamine Pt(IV) complex: [7(OH)M]

30% $H_2O_2$ (30 ml) was added to 5 g (12.99 mM) of 7M (malonato-1,4-butanediamine Pt(II) complex) dissolved in water (300 ml) and then, the resultant was stirred for 72 hours at room temperature. At this time, the reaction did not occur at temperature over 80° C. It deems because Pt complex having malonate as a leaving ligand contains a weak hydrogen bond therein and its 7-membered ring conformation is chair form which is relatively unstable than the twisted form, and thus the hydrogen bond is broken when the reaction temperature becomes high. Therefore, 7(OH)M may not be obtained.

The resultant solution was concentrated to be 5 ml under a condition of reduced pressure and then, added with cooled methanol to generate precipitate. After filtration, the precipitate was washed with methanol and ether, and dried under reduced pressure at 60° C. to generate a white precipitate (3.67 g).

| | |
|---|---|
| Yield | 67.43% |
| IR(KBr,cm$^{-1}$) | 3525, 3205, 1660, 1370, 975, 753, 569 |
| $^1$H-NMR(D$_2$O) | 1.8–2.0(4H), 2.8(2H), 2.9(4H), 3.0(2H) |

Elemental analysis:

Calc. for $C_7H_{16}N_2O_6Pt$

C; 20.05%, H; 3.82%, N; 6.68%,

Found for C; 19.98%, H; 3.79%, N; 6.62%,

According to the result of analyzing IR, a strong vibration due to O—H bond appeared around 3500 cm$^{-1}$, a strong absorption by C=O bond appeared around 1660 cm$^{-1}$ and a strong absorption due to C—O bond appeared around 1370 cm$^{-1}$.

Referring to the result of Elemental analysis, the content ratio of carbon, hydrogen and nitrogen in the molecule detected by experiment was substantially identical to its calculated value.

EXAMPLE 5

Synthesis of trans-Acetato,malonato-1,4-butanediamine Pt(IV) complex: [7(Ac)M]

Except using 1.5 g (3.58 mM) of 7(OH)M (trans-Hydroxy,malonato-1,4-butanediamine Pt(IV) complex), the same method as the one used for synthesizing 7(Ac)Cl was repeated. The resultant solution was re-crystalized using a water-methanol mixture wherein the ratio of water:methanol was 2:3, to generate a white acicular crystal (0.98 g).

| | |
|---|---|
| Yield | 54.42% |
| IR(KBr,cm$^{-1}$) | 3444, 3172, 3049, 1660, 1362, 709, 532 |
| $^1$H-NMR(D$_2$O) | 2.95–2.75(8H), 1.95–1.8(8H) |
| $^{13}$C-NMR(D$_2$O) | 188, 183.9, 179.8, 179.2, 49.2, 48.7, 28.4, 28.1, 24.9 |

Elemental analysis:

Calc. for $C_7H_{16}N_2O_6Pt$

C; 26.24%, H; 3.98%, N; 5.57%,

Found for C; 26.19%, H; 3.95%, N; 5.53%,

According to the result obtained by IR, the O—H peak around 3500 cm$^{-1}$ was disappeard which was shown in 7(OH)M, and a strong absorption peak by C=O vibration was observed at 1660 cm$^{-1}$ and peaks by C—O vibration were observed at 1370 cm$^{-1}$ and 1278 cm$^{-1}$.

$^1$H-NMR using D$_2$O solvent was performed, but peaks were not clear.

Referring to $^{13}$C-NMR spectra, 4 carbons consisting of carbonyl group weredetectedat 179.2, 179.8, 183.8 and 187.9 ppm, respectively and carbons consisting of alkyl group were detected around 24.9–49.2 ppm.

EXAMPLE 6

Synthesis of trans-Trifluoroacetato,malonato-1,4-butanediamine Pt(IV) complex; [7(TF)M]

Except using 1.5 g (3.58 mM) of 7(OH)M [trans-Hydroxy,malonato-1,4-butanediamine Pt(IV) complex], the same method as the one used for synthesizing 7(TF)Cl was repeated. The resultant solution was re-crystalized using methanol to generate a transparent cube type of crystal (1.45 g).

| | |
|---|---|
| Yield | 66.29% |
| IR(KBr,cm$^{-1}$) | 3440, 3200, 3089, 1716, 1651, 1368, 1161, 739, 523 |
| $^1$H-NMR(CD$_3$OD) | 3.6(2H), 2.9(4H), 2(4H) |
| $^{13}$C-NMR(CD$_3$OD) | 176.4, 49.5, 49.3, 49.2, 49, 48.8, 48.6, 48.5, 47.4, 47.3, 26.5 |

Elemental analysis

Calc. for $C_{11}H_{14}N_2O_8F_6Pt$

C; 21.6%, H; 2.29%, N; 4.58%,

Found for C; 21.58%, H; 2.30%, N; 4.57%,

The structure of the obtained compound was confirmed by IR, NMR, Elemental analysis and X-ray diffraction.

According to the result of IR, as 7(Ac)M, the O—H peak around 3500 cm$^{-1}$ disappeared, a strong absorption peak by C=O bond neighboring fluorine appeared at 1716 cm$^{-1}$, a strong absorption peak by C=O bond consisting of malonate group was observed at 1651 cm$^{-1}$, a strong absorption peak by C—O bond was shown at 1368 cm$^{-1}$ and a strong absorption peak by C—F bond was shown at 1161 cm$^{-1}$.

Referring to $^1$H-NMR spectra analysis using CD$_3$OD as a solvent, a peak by 4 hydrogens consisting of 2 methyl groups farthest from amine was shown around 2 ppm, a peak by 4 hydrogens consisting of 2 methyl groups neighboring the amine was shown around 2.9 ppm, and a peak by 2 hydrogens bonding to the carbon positioned between carbonyl groups was shown around 3.6 ppm.

According to $^{13}$C-NMR spectra analysis, most peaks transferred to the direction of a high magnetic field between 47.3–49.5 ppm, because of electrophilic influence of fluorine atom.

Elemental analysis result showed that the content ratio of carbon, hydrogen and nitrogen consisting of the molecule detected by experiment was substantially identical to the theoretical value.

Figure 3:
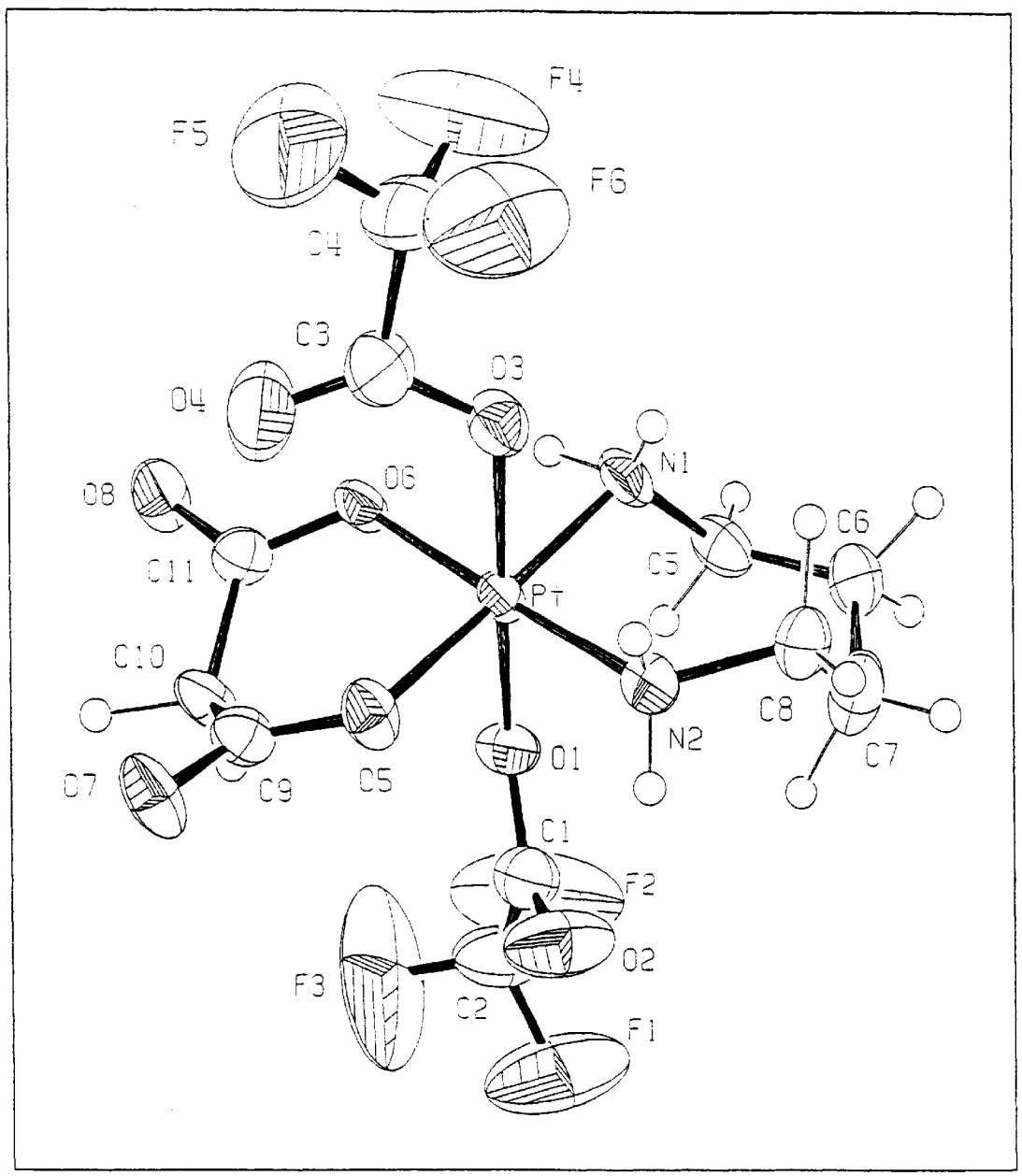

FIG. 3 shows the crystal structure obtained using X-ray diffraction method. As shown in FIG. 3, [7(TF)M] contains also hydrogen bonds between N1—H and O6, and between N2—H and O2. Apart from 7(Ac)Cl or 7(TF)Cl, the conformation of 7-membered ring of [7(TF)M] is chair form and the conformation of 6-membered ring consisted of Pt and malonate is boat form.

The following Table 3 shows bond lengths and bond angles between Pt and its neighboring elements, which is detected by X-ray diffraction method.

TABLE 3

Bond Length and Angle of trans-ditrifluoroacetato, malonato-(1,4-butanediamine)Pt(IV) complex

| | |
|---|---|
| Pt-O(3) | 1.979(5) |
| Pt-O(1) | 1.997(5) |
| Pt-O(6) | 2.003(5) |
| Pt-O(5) | 2.009(5) |
| Pt-N(2) | 2.024(6) |
| Pt-N(1) | 2.035(6) |
| O(3)-Pt-O(1) | 175.2(9) |
| O(3)-Pt-O(6) | 90.7(2) |
| O(1)-Pt-O(6) | 86.7(2) |
| O(3)-Pt-O(5) | 92.5(2) |
| O(1)-Pt-O(5) | 91.9(2) |
| O(6)-Pt-O(5) | 97.4(8) |
| O(3)-Pt-N(2) | 85.5(2) |
| O(1)-Pt-N(2) | 97.1(2) |
| O(6)-Pt-N(2) | 176.2(2) |
| O(5)-Pt-N(2) | 82.3(2) |

TABLE 3-continued

Bond Length and Angle of trans-ditrifluoroacetato, malonato-(1,4-butanediamine)Pt(IV) complex

| | |
|---|---|
| O(3)-Pt-N(1) | 84.8(2) |
| O(1)-Pt-N(1) | 90.8(2) |
| O(6)-Pt-N(1) | 82.8(2) |
| O(5)-Pt-N(1) | 177.3(2) |
| N(2)-Pt-N(1) | 97.4(3) |

Wherein, the reliability (R) of X-ray diffraction analysis is 0.035.

PREPARATION OF PHARMACEUTICAL COMPOSITION

The pharmaceutical composition according to the present invention contains the compound represented by the Chemical Formula 3 as a main component.

The pharmaceutical composition according to the present invention can be used as an oral composition with pharmaceutically acceptable carrier, or can be used as an injection composition with appropriate solvent or diluent.

(1) Oral Composition

The Pt(IV) complex according to the present invention is very stable enough not to be destroyed by gastric acid, thus enabling to do oral administration. When used as an oral composition, it can be administered in the form of capsule or tablet. In the case of capsule, a conventional excipient such as starch, lactose, talc, magnesium stearate and so on can be used. Also, in the case of tablet, since the tablet consists of granules, a conventional excipient can be used.

In addition, a conventional carrier can be added to the composition and as an additive, starch, crystal cellulose, hydroxypropylmethylcellulose, polyethyleneglycol, lactose, polyvinylpyrrolydone or glyceryl behanate can be used together. Also, as a diluent, glucose, dried lactose, Fast-flolactose, dehydrated lactose, sucrose, starch, starch 1500, calcium hydrogen phosphate, emcompress or avicel can be used; as a wet binder or a granule solution, water, ethanol, gum arabic, tragacanth, gelatin solution, starch paste solution, glucose syrup, sucrose syrup, povidone or cellulose derivatives can be used; as a lubricant, polyethyleneglycol 4000, 6000, 8000, lauryl sodium sulfate, lauryl magnesium sulfate, sodium benzoate, polyethylene monostearate, glyceryl triacetate, magnesium stearate, zinc stearate, calcium stearate, stearic acid, talc, hardened vegatable oil, liquid paraffin, paraffin derivatives or wax can be used; as a fluidizing agent, starch, talc, silicon dioxide, silicate, magnesium carbonate or magnesium oxide can be used; as an adhesion inhibitor, starch or talc can be used; and as an additive for control release, hydroxypropylmethylcellulose, hydroxypropylcellulose, hydroxyethylcellulose, ethylcellulose, methylcellulose, carboxymethylcellulose, polyacrylic acid, acrylic acid, acrylate derivatives, poly vinylpyrrolydone or polyethyleneglycol can be used.

(2) Injection Composition

When Pt(IV) complex according to the present invention is used as an injection composition, as a solvent, alcohol (such as ethanol, benzylalcohol, propyleneglycol and glycerine), higher fatty acid ester (such as ethyl oleinate) and the like are preferred; as a diluent, phosphate buffer saline (PBS), 0.9% NaCl (saline) and the like are preferred; and as an antiseptic, sodium benzoate, methylparaben, propylparaben and the like can be added.

For example, when the pharmaceutical composition according to the present invention is preprared as an injection, first, the Pt(IV) complex according to the present invention is subject to frozen-dry to be a form of powder. Then, the powder dissolves in solvents such as alcohol, dilutes with phosphate buffer saline (PBS) or 0.9% NaCl (saline) and then administers to a human body.

EXPERIMENAL ON ANTI-CANCER ACTIVITY

In order to examine anti-cancer activity of Pt(IV) complexes according to the present invention, MTT, i.e., [3-(4, 5-dimethylthiazol-2-yl)-2,5-diphenyltetrazolium bromide] assay was performed on HL60 and L1210 which are leukemic cell of human and mice, respectively.

MTT assay is a quantitative color analysis based on that mitochondrial dehydrogenase, one of cell enzymes, changes yellow water-soluble MTT into deep-blue water-insoluble formazan, and the amount of the generated formazan is proportioned to active cell numbers.[122-124]

(1) Reagent and Aapparatus

HL60 and L1210, suspended leukemic cells of humans and mice, respectively are used as cancer cells for determining the anti-cancer activity of the Pt (IV) complex according to the above Examples. They were obtained by cultivating the frozen cells alloted from Korean Cell Line Bank.

RPMI 1640 culture medium, 1000 unit/ml of penicillin-streptomycin, fetal bovin serum (hereinafter, referred to be FBS), phosphate buffer saline (hereinafter, referred to be PBS) were purchased from Gibco. Cisplatin and MTT reagent were purchased from Sigma, $CO_2$ gas was purchased from Dong-A Gas Incorporation, and the other reagents were those for cell culture or premium grade.

The number of cell was counted by optical microscopy (Olympus CK2) using hematocytometer and, as ELISA plate reader, Dynatech MR5000 was used.

(2) Cell Culture

Cells were subject to subculture at the interval of 2–3 days at 37° C. in the presence of 5% $CO_2$ in RPMI 1640 culture medium controlled to contain 1% penicillin-streptomycin (10,000 unit/ml) and 10% FBS, with keeping the cell number between $2\times10^5$/ml–$5\times10^5$/ml.

(3) Reagent and Preparation of Pharmaceutical Composition

Pt (IV) complexes prepared by the Examples of the present invention were used as pharmaceutical compounds. Among them, a water-soluble compound was used as it was, and a water-insoluble compound was used after dissolving in DMSO or 95% ethanol, adding PBS to be 2 mM concentarion, filtering with $0.2\mu$ syringe filter to be sterile state and performing serial-dilution with a culture medium to control predetermined concentrations. The final concentration of DMSO or 95% ethanol in cell culture medium was controlled to be below 0.1%.

MTT reagent was used after dissolving it in PBS and filtering it using $0.2\mu$ pfilter to be in sterile state.

(4) Experimental Method

HL60 and L1210 cells were put into 96-well plate in the amount of $10^4$/well and then stabilized for a half hour at 37° C. in the presence of 5% $CO_2$. Then, $10^{-4}$M–$10^{-7}$ M/ml of Pt (II) complex and Pt (IV) complex were added to each well by 100 $\mu$l.

After cultivating HL60 cell at 37° C. in the presence of 5% $CO_2$ for 72 hours and L1210 for 48 hours, MTT reagent (2 mg/ml) was added 50 $\mu$l/well, and an additional cultivation was performed at 37° C. in the presence of 5% $CO_2$ for 4 hours. Then, after centrifuging the resultant at 2000 rpm for 5 minites, the supernatant was removed by 170 $\mu$l/well.

Then, after adding DMSO 150 $\mu$l/well, the resultant was laid at 40° C. for 30 minutes and stirred for 3 minutes. Then, absorption test using ELISA reader was performed at 570 nm.

For calibration, a blank test was performed on the same 96-well plate under the same condition.

The above-described experiment was performed on more than 3 wells under the same condition with different concentration, and the same experiment was repeated over 3 times.

(5) Test Result

The following Tables 4 to 6 show MTT assay results.

TABLE 4

| | Anti-cancer Activity of L1210 in vitro | | | | | | |
|---|---|---|---|---|---|---|---|
| | 7(Ac)Cl | 7(TF)Cl | 7(Ac)M | 7(TF)M | 7(OH)Cl | 7(OH)M | 7 Mal |
| 100 $\mu$M | 2.2 | 0.5 | 20.6 | 17.1 | 20.5 | 40.5 | 20.5 |
| 50 $\mu$M | 5.1 | 1.6 | 25 | 20 | 30.5 | 55.1 | 26.1 |
| 10 $\mu$M | 9.6 | 2.8 | 60 | 49 | 62.5 | 76.8 | 55 |
| 5 $\mu$M | 31.1 | 25 | 65.5 | 59 | 66 | 80 | 68 |
| 1 $\mu$M | 59.5 | 55 | 78 | 72 | 83.1 | 88.5 | 80.1 |
| 0.5 $\mu$M | 69 | 66.2 | 84 | 78 | 85.5 | 92 | 84.8 |
| 0.1 $\mu$M | 82 | 78.5 | 91 | 88 | 91.2 | 97 | 93 |
| 0.05 $\mu$M | 86.1 | 83.2 | 93 | 93 | 92.8 | 101.1 | 95 |
| 0.01 $\mu$M | 90.4 | 88.5 | 95 | 93.5 | 94 | 96 | 91 |

Wherein, the concentration unit of Pt(IV) complex in culture medium is $\mu$M/ml; and Cell Growth is calculated by the following equation.

$$\text{Cell growth}(\%) = \frac{OD \text{ average in experimental group}}{OD \text{ average in control group}} \times 100$$

wherein, OD(optical density) represents adsorption by ELISA Reader.

TABLE 5

Anti-cancer Activity of HL60 in vitro

| | 7(Ac)Cl | 7(TF)Cl | 7(Ac)M | 7(TF)M | 7(OH)Cl | 7(OH)M | 7 Mal |
|---|---|---|---|---|---|---|---|
| 100 $\mu$M | 5 | 0 | 20 | 15.1 | 19 | 37.4 | 20 |
| 50 $\mu$M | 5 | 0 | 20 | 24.5 | 27.5 | 52.9 | 27 |
| 10 $\mu$M | 15.9 | 2 | 60 | 45 | 58.4 | 70.5 | 57 |
| 5 $\mu$M | 29.7 | 20 | 64.8 | 55 | 60 | 75.4 | 63.2 |
| 1 $\mu$M | 55.9 | 53.5 | 72 | 68 | 80.1 | 86.9 | 78.8 |
| 0.5 $\mu$M | 65 | 60 | 85 | 70 | 83.5 | 97 | 82.6 |
| 0.1 $\mu$M | 80 | 75.2 | 87 | 87 | 91.8 | 98 | 89 |
| 0.05 $\mu$M | 84.5 | 78.9 | 90 | 90 | 90.8 | 100 | 89 |
| 0.01 $\mu$M | 90.8 | 82.5 | 96 | 90.5 | 92 | 103 | 92 |

Wherein, the concentration unit of Pt(IV) complex in culture medium is $\mu$M/ml; and Cell Growth is calculated by the following equation.

$$\text{Cell growth}(\%) = \frac{OD \text{ average in experimental group}}{OD \text{ average in control group}} \times 100$$

wherein, OD(optical density) represents absorption by ELISA Reader.

TABLE 6

$IC_{50}$ in L1210 Cell and in HL60 Cell

| | L1210($\mu$M/ml) | HL60($\mu$M/ml) |
|---|---|---|
| CDDP | 2.86 | 2.74 |
| 7(Ac)Cl | 1.49 | 1.28 |
| 7(TF)Cl | 0.96 | 0.69 |
| 7(Ac)M | 14.44 | 12.17 |
| 7(TF)M | 8.72 | 6.72 |
| 7 Cl | 2.01 | 1.83 |
| 6 Cl | 19.26 | 16.05 |
| 5 Cl | 11.04 | 11.7 |
| 7(OH)Cl | 17.38 | 13.84 |
| 7(OH)M | 64.42 | 49.7 |
| 7 Mal | 15.02 | 13.8 |

Wherein, 7Cl represents cis-dichloro-1,4-butanediamine Pt(II) complex which has 7-membered ring structure;

6Cl represents cis-dichloro-1,3-propanediamine Pt(II) complex which has 6-membered ring structure;

5Cl represents cis-dichloro,ethylenediamine Pt(II) complex which has 5-membered ring structure; and $IC_{50}$ represents the amount of an anti-cancer agent required to inhibit the cell-growth to be 50%.

(6) Analysis of Experimental Result

EXAMPLE 7

Anti-cancer Activity of 7(TF)Cl and 7(Ac)Cl

Figure 8:
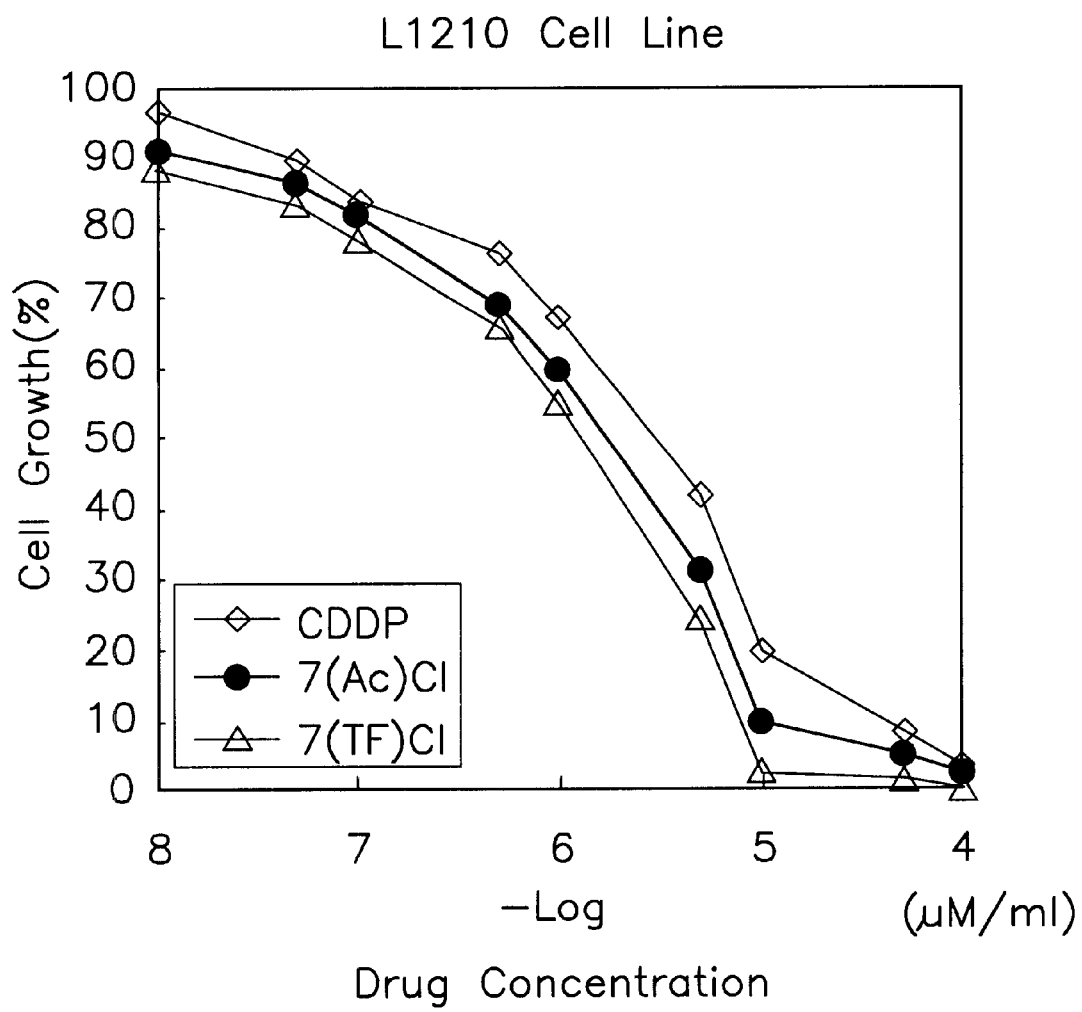
FIG. 8 is a chart showing anti-cancer activities $IC_{50}$ of cisplatin(CDDP), 7(TF)Cl and 7(Ac)Cl, according to the example 7 of the present invention.

First, in L1210 cell, anti-cancer activities $IC_{50}$ of cisplatin (CDDP), 7(TF)Cl and 7(Ac)Cl are detected and shown in the FIG. 8. As shown in the FIG. 8, anti-cancer activity of 7(TF)Cl was the highest as $IC_{50}$ is 0.96 $\mu$M/ml, and $IC_{50}$ of 7(Ac)Cl was 1.49 $\mu$M/ml.

Considering $IC_{50}$ of cisplatin(CDDP) used clinically at present is 2.86 $\mu$M/ml, $IC_{50}$ of 7(TF)Cl and 7(Ac)Cl are extremely lower, which indicates their anti-cancer ability are superior to cisplatin(CDDP).

Figure 9:
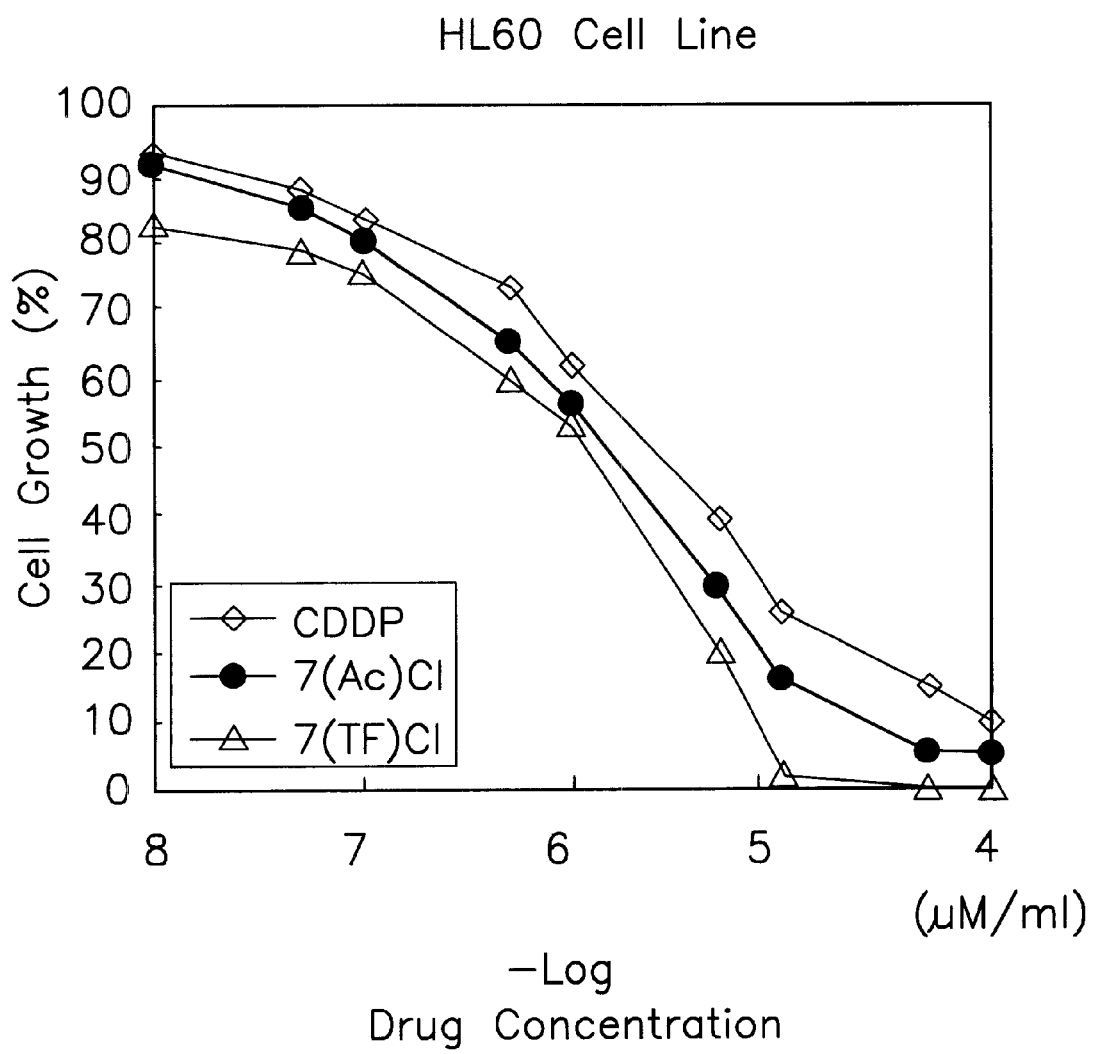
FIG. 9 is a chart showing anti-cancer activities $IC_{50}$ of cisplatin(CDDP), 7(TF)Cl and 7(Ac)Cl in HL60 cell, according to the example 7 of the present invention.

The FIG. 9 shows anti-cancer activities $IC_{50}$ of cisplatin (CDDP), 7(TF)Cl and 7(Ac)Cl in HL60 cell. As shown in the FIG. 9, while $IC_{50}$ of cisplatin(CDDP) was 2.74 $\mu$M/ml, $IC_{50}$ of 7(TF)Cl and 7(Ac)Cl were 1.28 $\mu$M/ml and 0.69 $\mu$M/ml, respectively. Accordingly, it shows that the anti-cancer activity of 7(TF)Cl and 7(Ac)Cl are superior to that of cisplatin.

EXAMPLE 8

Anti-cancer Activity of 7(Ac)M and 7(TF)M

Figure 10:
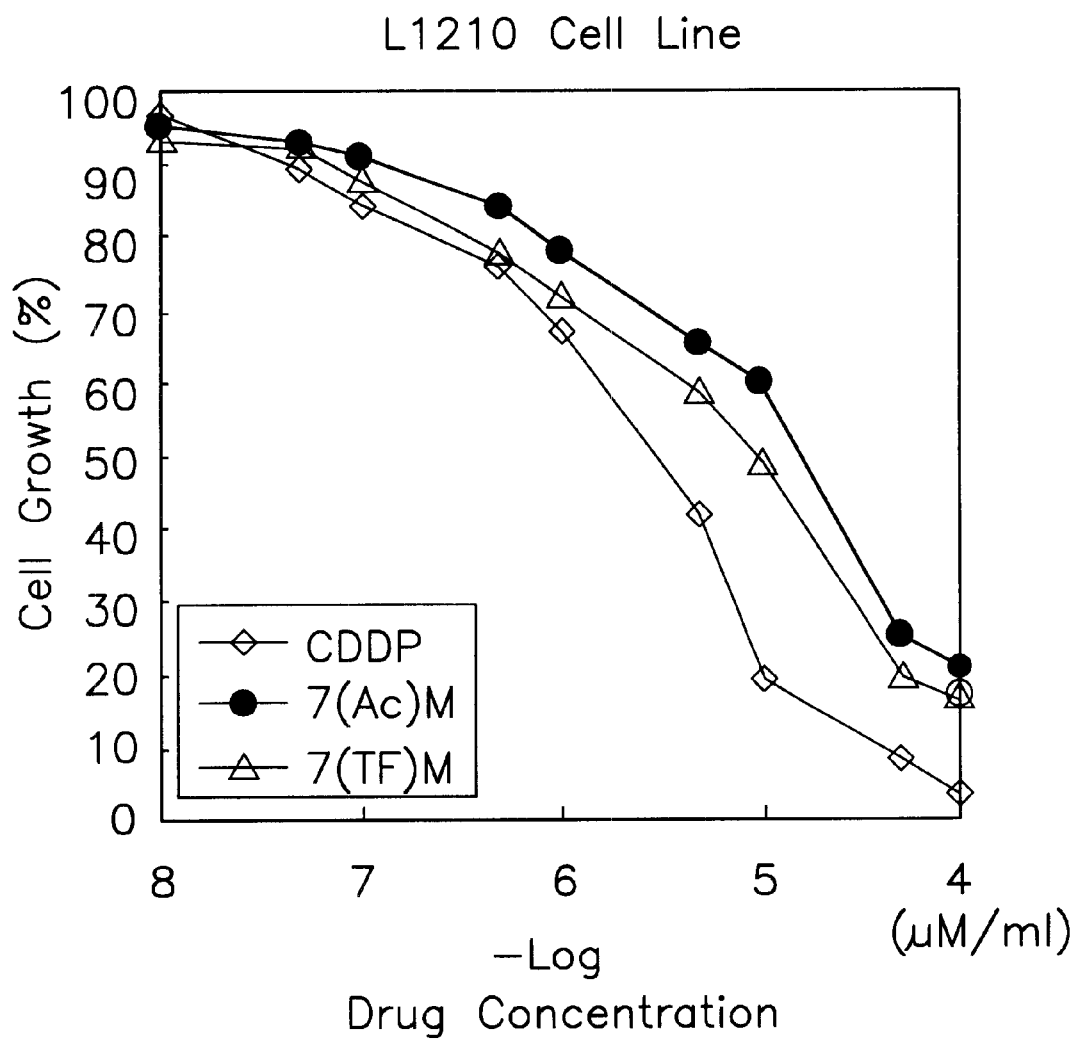
FIG. 10 is a chart showing anti-cancer activities $IC_{50}$ of cisplatin(CDDP), 7(Ac)M and 7(TF)M, according to the example 8 of the present invention.

Anti-cancer activity tests of cisplatin(CDDP), 7(Ac)M and 7(TF)M were performed on L1210 cell, and the result was shown in the FIG. 10.

As shown in the FIG. 10, $IC_{50}$ of 7(Ac)M and 7(TF)M were 14.44 $\mu$M/ml and 8.72 $\mu$M/ml, respectively, which were 3 to 4.5 times higher than that of cisplatin. However, it is lower than that of carboplatin, used clinically as the $2^{nd}$ generation Pt complex, whose $IC_{50}$ is about 10 times higher than that of cisplatin. (J. Med. Chem. 1994, vol.37, No.10, 1471–1485).

Figure 11:
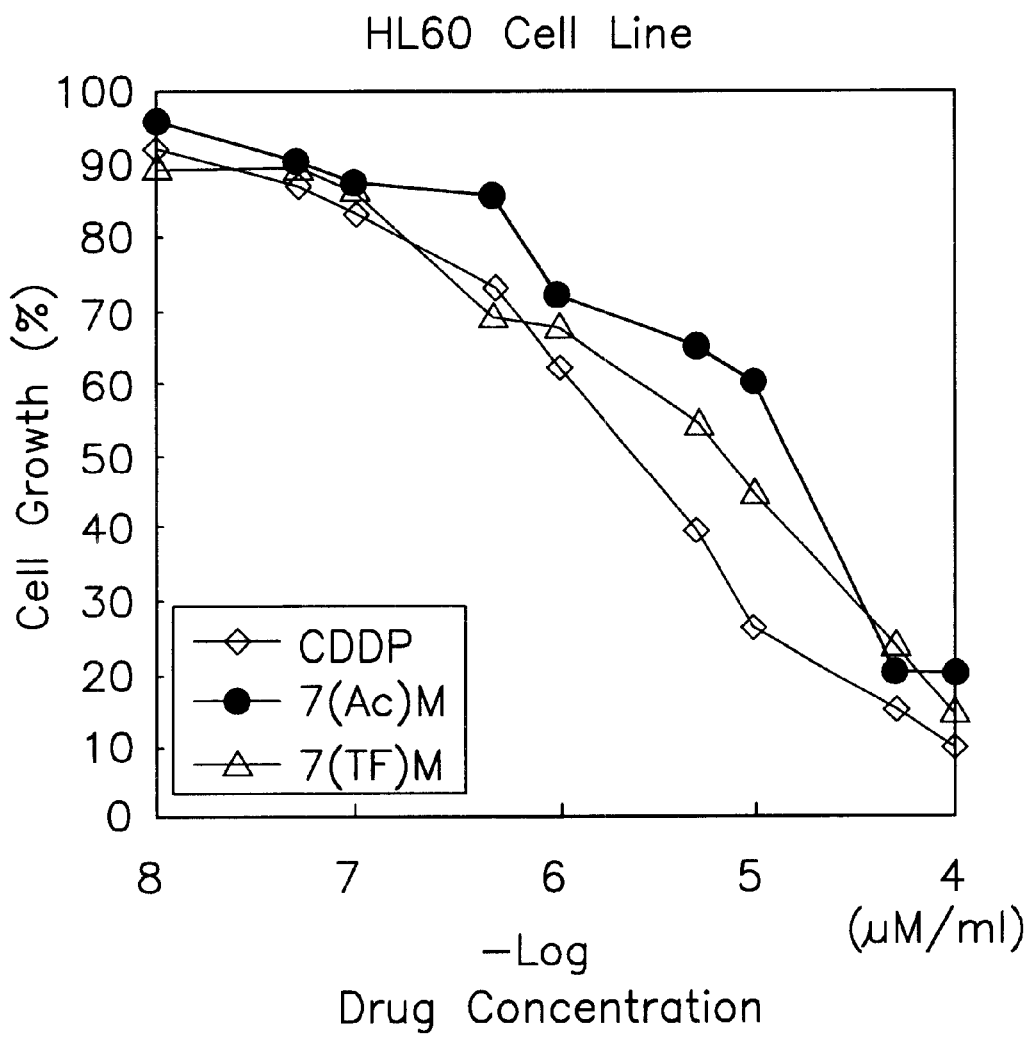
FIG. 11 is a chart showing anti-cancer activities $IC_{50}$ of cisplatin(CDDP), 7(Ac)M and 7(TF)M in HL60 cell, according to the example 8 of the present invention.

Then, anti-cancer activity tests of cisplatin(CDDP), 7(Ac)M and 7(TF)M were performed on HL60 cell, and the result was shown in the FIG. 11.

As shown in the FIG. 11, the result of anti-cancer activity test on HL 60 was similar to that of L1210. That is, even though the $IC_{50}$ of 7(Ac)M and 7(TF)M are higher than that of cisplatin, it is relatively lower than carboplatin.

In the other side, 7(Ac)M and 7(TF)M have superior anti-cancer characteristics to that of cisplatin in that it can alleviate side-effects such as nephrotoxicity. In addition, because 7(Ac)M and 7(TF)M show good activity on cancer cell resistant to cisplatin or carboplatin, they are useful as substitutes thereof.

EXAMPLE 9

Anti-cancer Activity of 7(OH)Cl and 7(OH)M

Figure 12:
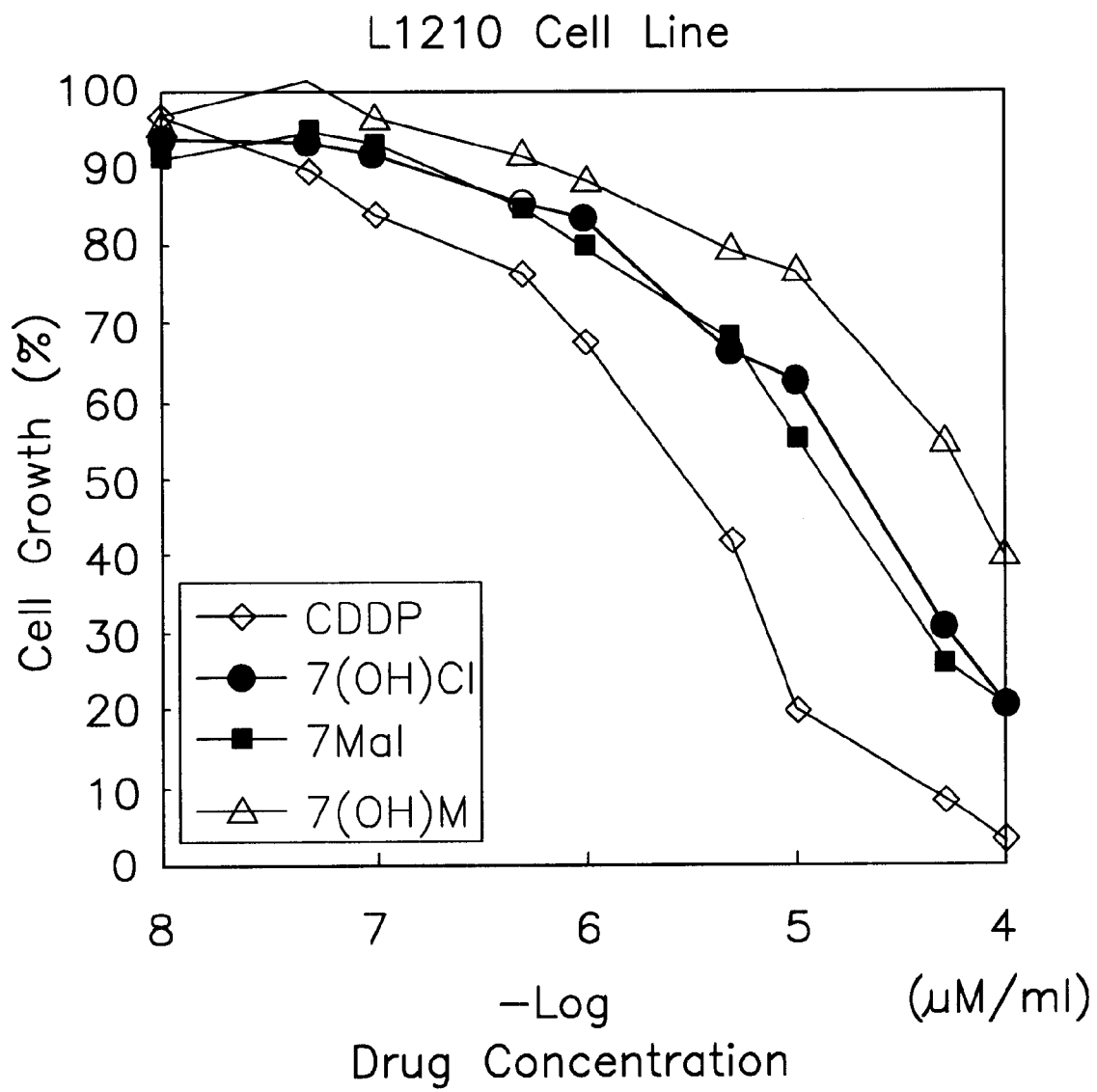
FIG. 12 is a chart showing anti-cancer activity test of 7(OH)Cl and 7(OH)M were performed on L1210 cell, according to the example 9 of the present invention.
Figure 13:
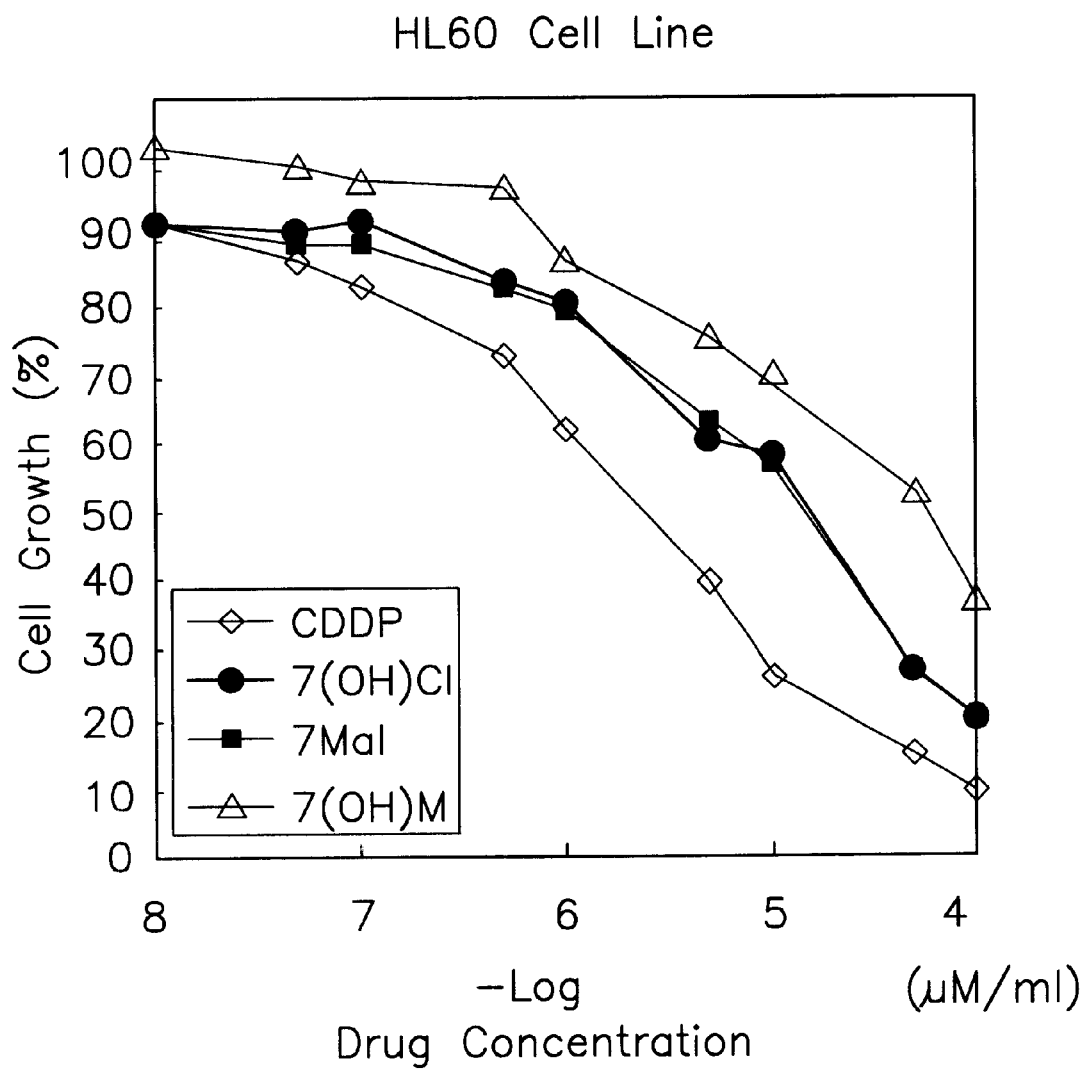
FIG. 13 is a chart showing anti-cancer activity test of 7(OH)Cl and 7(OH)M were performed on HL60 cell, according to the example 9 of the present invention.

Anti-cancer activity tests of 7(OH)Cl and 7(OH)M were performed on L1210 cell and HL60, respectively, and the results were shown in the FIGS. 12 and 13.

As shown in the FIGS. 12 and 13, these Pt(IV) complexes showed lower anti-cancer activity than that of cisplatin.

However, 7(OH)Cl and 7(OH)M are useful in that they can alleviate side-effects such as nephrotoxicity and have effectiveness to the cancer-cell resistant to cisplatin or carboplatin.

Furthermore, 7(OH)Cl and 7(OH)M are also useful as an intermediate materials for synthesizing 7(TF)Cl and 7(Ac)Cl.

The FIG. 14 is a bar graph showing $IC_{50}$ of novel Pt(IV) complexes according to the present invention and a conventional cisplatin.

NEPHROTOXICITY TEST (A) Serologic Analysis

In order to serologically analyze nephrotoxicity of various Pt complexes, after injecting each agent intraperitneally, blood was exsanguinated after 6 hours, 1 day, 3 days and 7 days, respectively. Then, serum was seperated f rom the blood to detect the values of BUN (Blood urea nitrogen), creatinine and uric acid.[133]

(1) Experimental Animals

As an experimental animal, male ICR mice each weighing about 25 g were purchased from Korean Experimental Animal Center. The experimental animals were bred in SPF(Specific Pathogen Free) room in Medical School of HanYang University, and food (purchased from SamYang) and water were supplied unrestrictedly.

The experimental animals were divided into a normal control group, a control group and an experimental group, and the experimental group was again divided into a cisplatin dispensing group, a 7(Ac)Cl treated group, a 7(TF)Cl treated group, a 7(Ac)M treated group, a 7(TF)M treated group and a 7FMN treated group.

Each groups comprised 20–22 mice, and each group was again divided into a 6 hour-treating group, a 1 day-treating group, a 3 day-treating group and a 7 day-treating group, which contains 5–6 mice, respectively.

(2) Treatment on the Experiment Animals 6 kinds of agents were used, i.e., cisplatin(CDDP), 7(Ac)Cl, 7(TF)Cl, 7(Ac)M, 7(TF)M and 7FMN. In dose per body weight 1 kg, cisplatin was 6 mg($IC_{50} \times 7$); 7(Ac)Cl was 6 mg($IC_{50} \times 8$); 7(TF)Cl was 5.3 mg($IC_{50} \times 8$); 7(Ac)M was 58.8 mg($IC_{50} \times 8$); 7(TF)M was 50.5 mg($IC_{50} \times 8$); and 7FMN was 88 mg($IC_{50} \times 8$).

First, a predetermined amount of agent was dissolved in DMSO or ethanol, and then PBS was added thereto to make the total volume be 6.6 ml. At this time, the content of DMSO or ethanol was controlled to be below 5%. Such amount does not reach 20 $\mu l$ per 1 mouse (30 g) and is extremly small enough not to affect experiment.

The agent dissolved in PBS was filtered using $0.2\mu$ syringe filter, sterilized, and injected into intraperitoneally. Then, after 6 hours, 1 day, 3 days and 7 days, exsanguination was performed.

(3) Detection of BUN (Blood Urea Nitrogen), Creatinine and Uric Acid

After seperating serum by centrifuging the blood exsanguinated from mice at 4,500 rpm for 15 minutes, the serum was kept at the temperature $-20°$ C. BUN (Blood urea nitrogen), creatinine and uric acid were detected using a biochemical automatic analyzing apparatus (Olympus reply, Japan) and average and standard deviation were calculated from the obtained data.

(4) Result of Experiment

The following Tables 7 to 9 show the detection result of BUN (Blood urea nitrogen), creatinine and uric acid.

Control group was dissolved in PBS and injected in dose of 6.6 ml/Kg. The result was represented as (average±standard deviation) of 5–6 ICR mice.

TABLE 7

BUN after the 1st time injection of Pt (IV) complex

| | Does(mg/kg) | 6 hour | 1 Day | 3 day | 7 Day |
|---|---|---|---|---|---|
| Control | — | 21.7 ± 3.7 | 22.9 ± 4.7 | 24.9 ± 3.4 | 19.5 ± 1.5 |
| Cisplatin | 6 mg | 23.1 ± 3.3 | 21.5 ± 2.5 | 20.7 ± 1.9 | 21.9 ± 3.9 |
| 7(Ac)Cl | 6 mg | 29.2 ± 1.8 | 19.4 ± 3.3 | 19.2 ± 2.8 | 22.1 ± 3.4 |
| 7(TF)Cl | 5.3 mg | 28.8 ± 6.4 | 23.1 ± 3.3 | 18.1 ± 2.3 | 20.7 ± 3.5 |
| 7(Ac)M | 58.8 mg | 24.0 ± 6.2 | 22.0 ± 4.1 | 22.4 ± 3.3 | 21.5 ± 5.1 |
| 7(TF)M | 50.5 mg | 22.1 ± 3.1 | 23.1 ± 4.8 | 22.9 ± 1.7 | 22.3 ± 1.7 |

TABLE 8

Creatinine after the 1st time injection of Pt (IV) complex

| | Does(mg/kg) | 6 hour | 1 Day | 3 day | 7 Day |
|---|---|---|---|---|---|
| Control | — | 21.7 ± 3.7 | 22.9 ± 4.7 | 24.9 ± 3.4 | 19.5 ± 1.5 |
| Cisplatin | 6 mg | 23.1 ± 3.3 | 21.5 ± 2.5 | 20.7 ± 1.9 | 21.9 ± 3.9 |
| 7(Ac)Cl | 6 mg | 29.2 ± 1.8 | 19.4 ± 3.3 | 19.2 ± 2.8 | 22.1 ± 3.4 |
| 7(TF)Cl | 5.3 mg | 28.8 ± 6.4 | 23.1 ± 3.3 | 18.1 ± 2.3 | 20.7 ± 3.5 |
| 7(Ac)M | 58.8 mg | 24.0 ± 6.2 | 22.0 ± 4.1 | 22.4 ± 3.3 | 21.5 ± 5.1 |
| 7(TF)M | 50.5 mg | 22.1 ± 3.1 | 23.1 ± 4.8 | 22.9 ± 1.7 | 22.3 ± 1.7 |

TABLE 9

Uric acid of after the 1st time injection of Pt (IV) complex

| | Does (mg/kg) | 6 hour | 1 Day | 3 day | 7 Day |
|---|---|---|---|---|---|
| Control | — | 2.1 ± 0.3 | 1.78 ± 0.4 | 2.28 ± 0.6 | 2.0 ± 0.4 |
| Cisplatin | 6 mg | 1.86 ± 0.4 | 2.86 ± 0.9 | 2.02 ± 0.6 | 1.92 ± 0.29 |
| 7(Ac)Cl | 6 mg | 2.18 ± 1.0 | 1.92 ± 0.4 | 1.88 ± 0.6 | 1.74 ± 0.5 |
| 7(TF)Cl | 5.3 mg | 2.2 ± 0.9 | 1.82 ± 0.5 | 2.22 ± 0.7 | 1.88 ± 0.3 |
| 7(Ac)M | 58.8 mg | 2.66 ± 0.7 | 2.34 ± 1.0 | 2.0 ± 1.5 | 1.52 ± 0.3 |
| 7(TF)M | 50.5 mg | 2.04 ± 0.3 | 1.8 ± 0.4 | 1.82 ± 0.4 | 1.96 ± 0.3 |

(5) Analysis

In order to serologically analyze nephrotoxicity of the Pt(IV) complex, dose of the Pt(IV) complex according to the present invention was determined based on cisplatin.

In the case of 1st time dispense of cisplatin, the dose in which toxicity is manifested or the manifested toxicity is recovered after a half-life period is 6 mg/kg and such amount is 7 times of $IC_{50}$.

The anti-cancer agents according to the present invention should have lower toxicity than cisplatin so that it can be a useful anti-cancer agent. Thus, the anti-cancer agents according to the present invention were administered in dose of 8 times of $IC_{50}$ per 1 kg of mouse body weight.

From the analysis of the sepearated serum, all of agents have no difference with the normal control group, which means that the 1st time dispense does not seriously damage the experimental animals and the Pt(IV) complexes according to the present invention, at least, do not have stronger nephrotoxicity than cisplatin.

(B) Electron Microscopic Findings (1) Experimental Method

In order to observe the ultra-structural changes of proximal renal tubule cells, a part of renal cortex of kidney was finely cut in the size of 1 $mm^3$, pre-fixed with 2% glutaraldehyde-2.5% paraformaldehyde solution, which is prepared with Millonig's phosphate buffer (pH 7.2) at 4° C. for 2–4 hours, and post-fixed with 1% osmium tetroxide for 2 hours, which is diluted with the same buffer solution. Then, after dehydrating the specimen according to ethanol-acetone concentration difference and embeding in Epon 812, it was made to be 2–5 μm thickness in thin section using ultramicrotome and temporarily stained with methylene blue to determine a proper site. Then, it was prepared tobe 60–80 nm thickness of the ultra-thin section, subject to double-staining with uranyl acetate and lead citrate, and observed with TEM (transmission electron microscope; Hitachi-600, Japan).

(2) Result

① Epithelium of proximal renal tubule in control group

Figure 4:
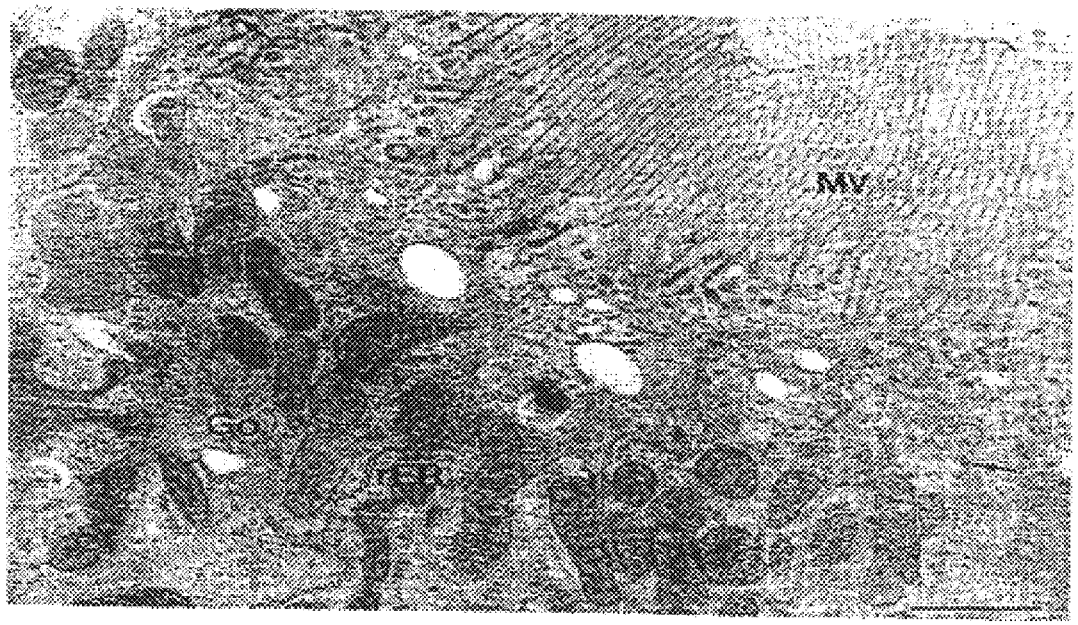
FIGS. 4 to 7b shows micro-structures of proximal tubule of mice novel Pt(IV) complexes according to the present invention injected i.p., which are detected by electron microscope, respectively.
Figure 4:
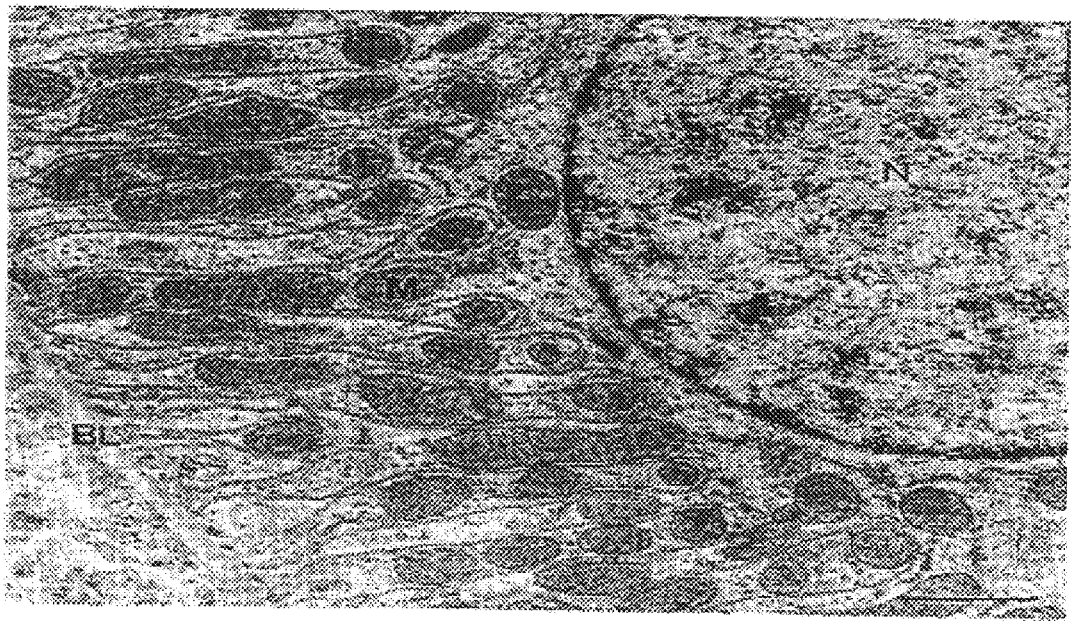

Proximal renal tubule epithelial cells are connected to neighboring cells by desmosome. Round nucleus is located in center of the cell. Numerous microvilli projected toward lumen and many endocytic vesicles and vacuoles in various sizes just beneath the microvilli are observed. In the cytoplasm mitochondria associated with rough endoplasmic reticulum, lysosome and Golgi complex composed of 3–4 layers of cisternae are found. At the bottom of the cytoplasm, well-developed basal folding disposed in parallel with mitochondria and rough endoplasm reticulum were observed (FIG. 4).

② Epithelium of proximal renal tubule in cisplatin treated group

Figure 5A:
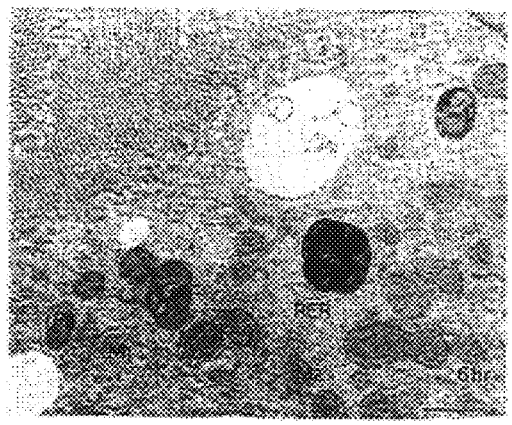
Figure 5A:
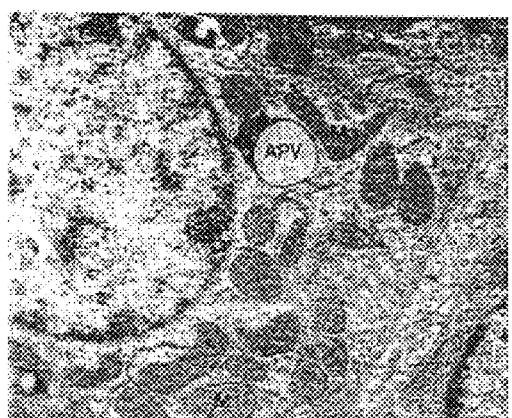
Figure 5A:
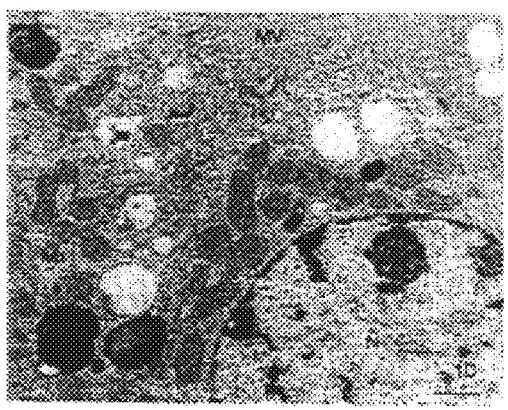
Figure 5A:

In the epithelium cell of proximal renal tubule cell in a group sacrificedafter 6 hours since i.p. injection of cisplatin, microvilli protruded toward lumen, many endocytic vesicles and vacuoles in the apical cytoplasm were observed. In the cytoplasm secondary lysosomes such as phagosome (Ph), autophagic vacuole (APV) and degenerated mitochondria which was dissolved in mitochondrial cristae (M1) or damaged by mitochondria membrane (M2) and horse shoe shaped mitochondria (M3), and rough endoplasm reticulum (RER) with detached ribosomes were found (FIG. 5a upper).

Figure 5B:
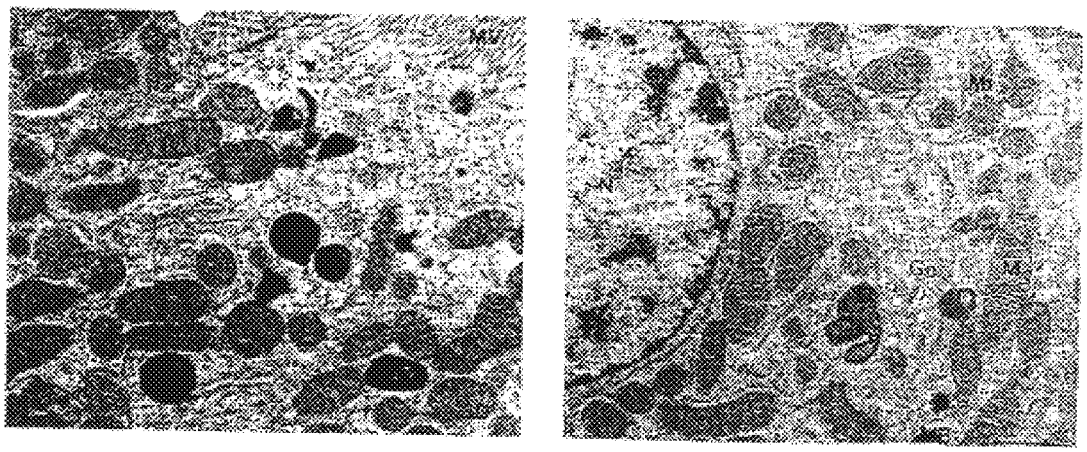
Figure 5B:
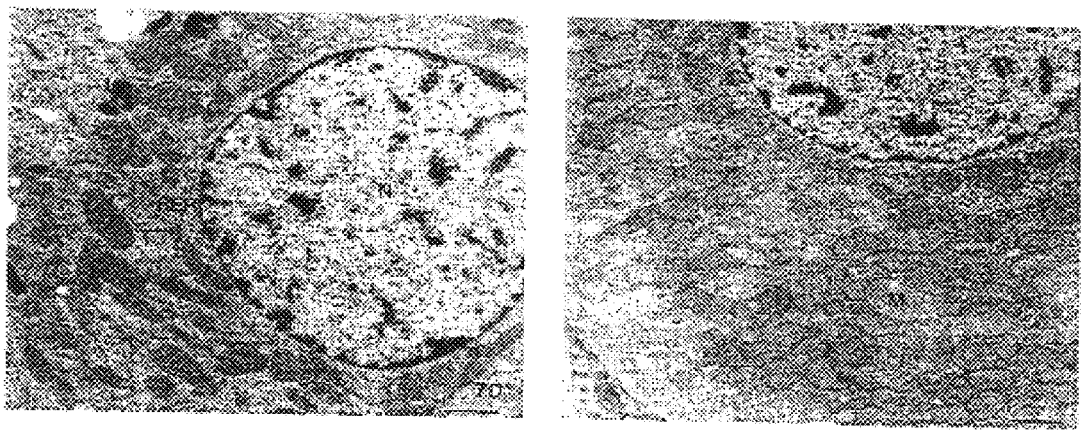

In the cytoplasm of proximal renal tubule cell in a group sacrificed after one day since i.p. injection of cisplatin, various secondary lysosomes such as autophagic vacuole (APV), phagosome (Ph), myeloid body (MB), mitochondria with dissolved cristae (M1), shape-changed damaged mitochondria (M2) and rough endoplasmic reticulum (RER) with detached ribosomes are found (FIG. 5b bottom).

In the cytoplasm of proximal renal tubule cell in a group sacrificed after 3 days since i.p. injection of cisplatin, many phagosomes (Ph) and myeloid bodies (MB), damaged mitochondria destructed double membrane or dissolved cristae, rough endoplasmic reticulum with segmented cisternae or detached ribosomes and Golgi complex with dilated cisternae were found (FIG. 5b upper).

In the cytoplasm of proximal renal tubule cell in a group sacrificed after 7 days since i.p. injection of cisplatin, many lysosomes in apical cytoplasm, numerous mitochondria associated with rough endoplasm reticulum, glycogen particles and well-developed basal folding are found (FIG. 5b bottom).

③ Epithelium of proximal renal tubule in 7(Ac)Cl treated group

Figure 6A:
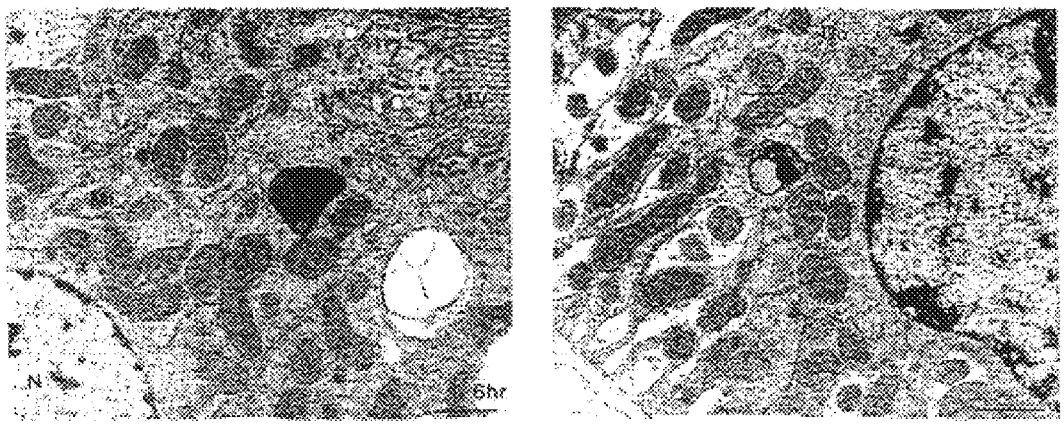
Figure 6A:
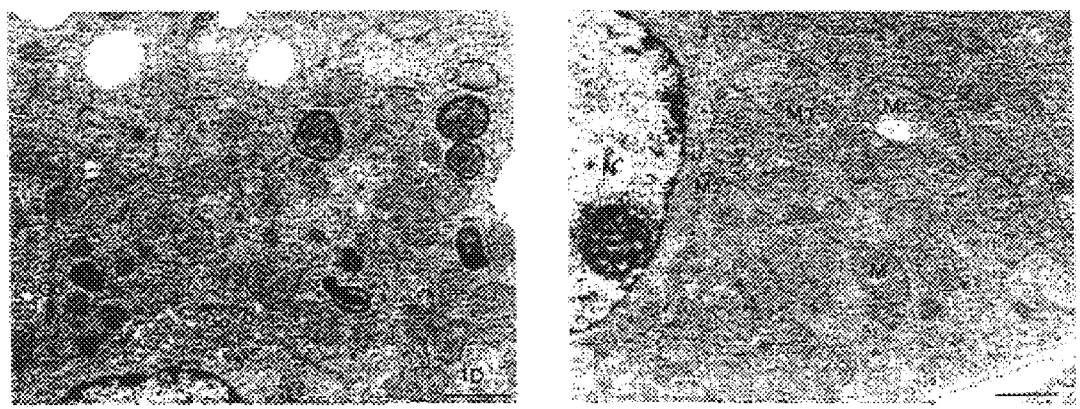

In the cytoplasm of the epithelial cell of proximal renal tubule in a group sacrificed after 6 hours since i.p. injection of 7(Ac)Cl, phagosome (Ph) and autophagic vacuole (APV), some mitochondria (M1) with dissolved cristae (M1) and Golgi complex adjacent to nucleus are observed (FIG. 6a upper).

In the cytoplasm of the epithelial cell of proximal renal tubule in a group sacrificed after one day since i.p. injection of 7(Ac)Cl, many myeloid bodies (MB), Golgi complex with atrophied cisternae, mitochondria with disrupted membrane (M1), shape-changed mitochondria (M2), mitochondria with dissolved cristae (M3) and rough endoplasm reticulum with defragmented or sacculated cisternae are found (FIG. 6a bottom).

Figure 6B:
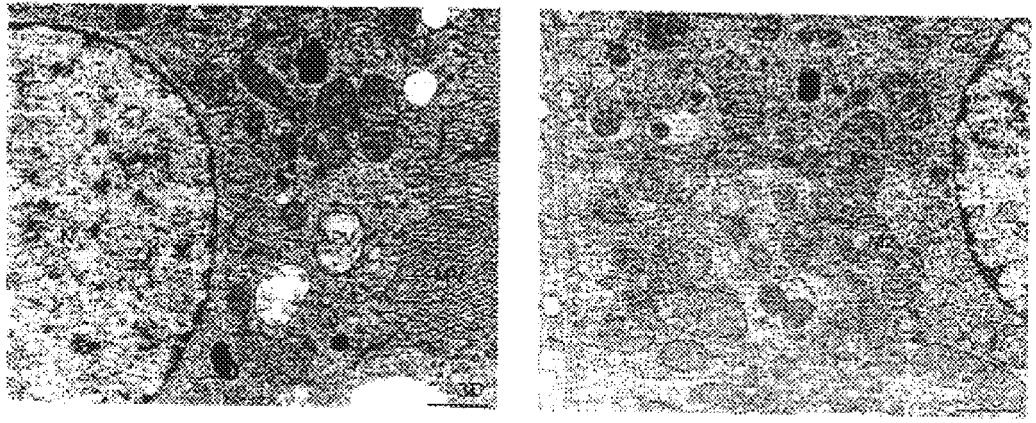
Figure 6B:
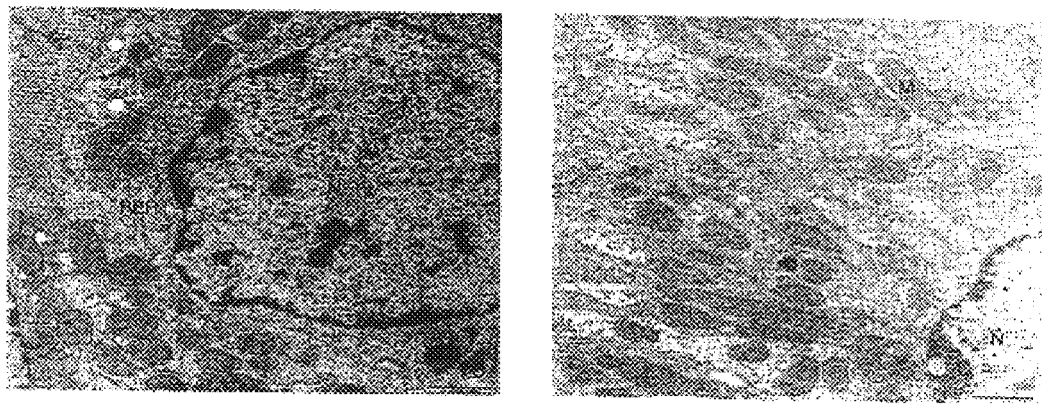

In the cytoplasm of the epithelial cell of proximal renal tubule in a group sacrificed after 3 days since i.p. injection of 7(Ac)Cl, secondary lysosomes such as myeloid body (MB), autophagic vacuole (APV), phagosome (Ph), rough endoplasm reticulum with segmented cisternae, atrophied Golgi complex and mitochondria with disrupted membrane (M1) or shape-changed mitochondria (M2) are observed (FIG. 6b upper).

In the cytoplasm of the epithelial cell in a group sacrificed after 7 days since i.p. injection of 7(Ac)Cl, numerous mitochondria associated with rough endoplasmic reticulum are found. In the basal portion of the cell well-developed basal folding in parallel with mitochondria are observed (FIG. 6b bottom).

④ Epithelium of proximal renal tubule in 7(TF)Cl treated group

Figure 7A:
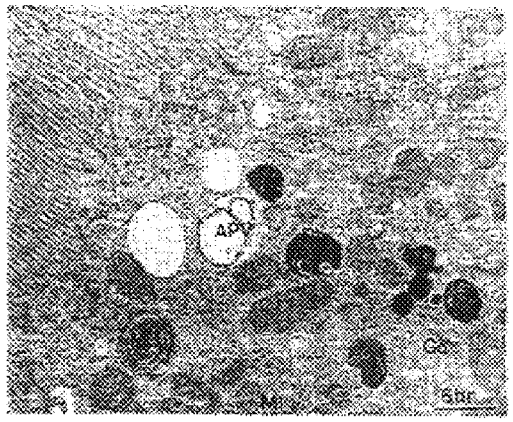
Figure 7A:
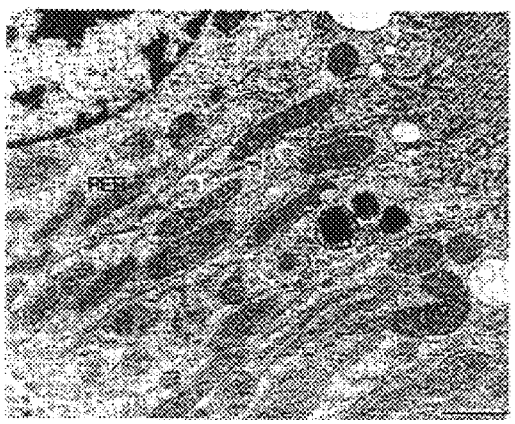
Figure 7A:
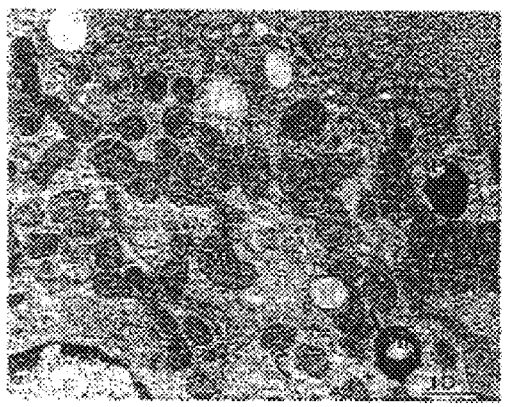
Figure 7A:
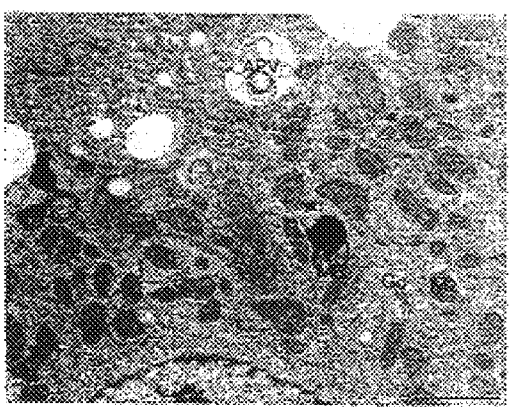

In the cytoplasm of the epithelial cell of proximal renal tubule in a group sacrificed after 6 hours since i.p. injection of 7(TF)Cl, secondary lysosomes such as myeloid body (MB), autophagic vacuole (APV), phagosome (Ph), atrophied Golgi complex (Go), damaged mitochondria (M2) and rough endoplasm reticulum with segmented or dialted cisternae are observed (FIG. 7a upper).

In the cytoplasm of the epithelial cell of proximal renal tubule in in a group sacrificed after one day since i.p. injection of 7(TF)Cl, phagosome (Ph), myeloid body (MB), autophagic vacuole (APV), atrophied Golgi complex (Go), mitochondria with swollen (M1) or dissolved (M2) cristae are found (FIG. 7a bottom).

Figure 7B:
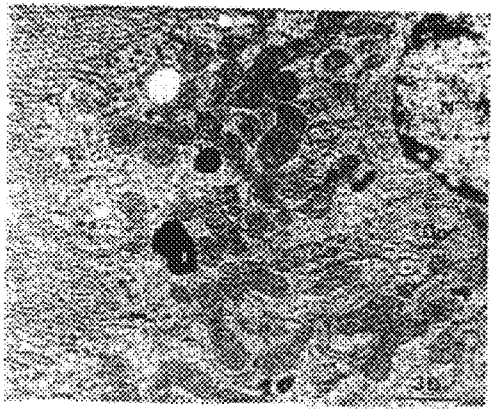
Figure 7B:
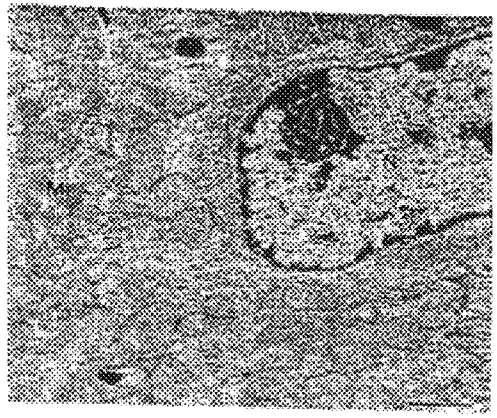
Figure 7B:
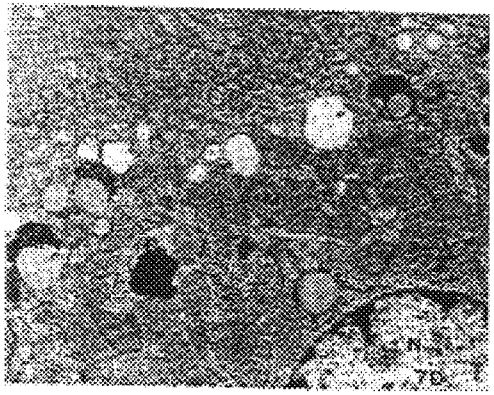
Figure 7B:
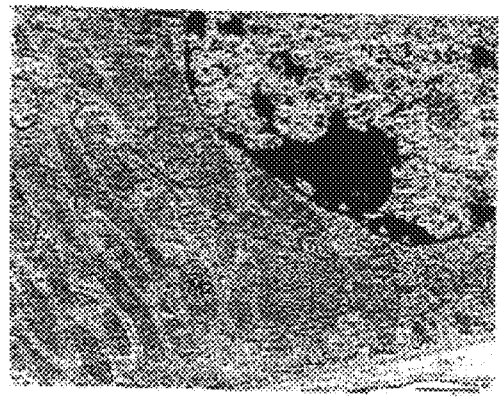

In the apical cytoplasm of the epithelial cell of proximal renal tubule in in a group sacrificed after 3 days since i.p. injection of 7(TF)Cl, phagosome (Ph) and lysosome (Ly) are located. In the cytoplasm atrophied Golgi complex (Go), mitochondria with disrupted membrane or dissolved cristae (M1) are observed (FIG. 7b upper).

In the apical cytoplasm of the epithelial cell of proximal renal tubule in in a group sacrificed after 7 days since i.p. injection of 7(TF)Cl, secondary lysosomes such as phagosome (Ph) and autophagic vacuole (APV) are found. In the cytoplasm shape-changed mitochondria (M1), mitochondria with disrupted membrane and dissolved cristae are observed (FIG. 7b bottom).

(3) Analysis

According to the results obtained from TEM experiment, in groups sacrificed after 6hours since i.p. injection of cisplatin and 7(TF)Cl, respectively, cytoplasmic organelles in the epithelial cell showed seriously damaged findings, and in groups sacrificed after 3 days since i.p. injection of ciplatin and 7(FT)Cl, most of cytoplasmic organelles were damaged, which means that these two agents have early cytotoxic effects to the epithelial cells of these two agents treated groups showed a similar ultra-structure to that of control group, which means that cytotoxic effects are decreased as time passess.

In case of 7(Ac)Cl treated group, after one day, cytoplasmic organelle damages such as the appearance of secondary lysosomes, damaged mitochodria and Golgi complex (Go) with atrophied cisternae are observed. However, these findings were recovered as time passed. Then, after 7 days, the ultra-structure in 7(Ac)Cl treated group becomes similar to that of control group. Such a phenomenon seems to be related to a decrease of the activity of acid phosphatase.

(C) Conclusion on Nephrotoxicity

According to the two kinds of experiments relating nephrotoxicity, i.e., serologic analysis and electron microscopic analysis, it can be said that Pt(IV) complex according to the present invention is less nephrotoxic than cisplatin.

That is, 7(Ac)Cl shows weaker toxicity than cisplatin, and 7(TF)Cl shows similar toxicity to the cisplatin. However, considering the doses of 7(Ac)Cl and 7(TF)Cl were 6 mg/kg and 5.3 mg/kg, respectively (8 times of $IC_{50}$) and the dose of cisplatin was 6 mg/kg (7 times of $IC_{50}$), it can be said that 7(TF)Cl is less toxic than cisplatin.

As described above, the anti-cancer compound according to the present invention (i) has 7-membered ring structure and thus shows an excellent anti-cancer activity. Also, it (ii) has chloride or malonate coordinate as a leaving ligand and thus shows desirable water-solubility and lipophilicity in body, and (iii) has an excellent bioavailibility and anti-cancer activity against cancer cells having resistance to cisplatin since it has a hexahedral structure with axial groups. Besides, it (iv) has less nephrotoxicityand (v) canbeorally administered and thus can alleviate patient's pain.

The followings are documents related to the present invention and a part of them were referenced in the specification.

1) Rosenberg, B., VanCamp, L., Krigas, T. L.: Inhibition of cell division in *Escherichia coli* by electrolysis products from a platinum electrode. Nature, 205, 698 (1965)
2) Rosenberg, B., VanCamp, L., Trosko, J. E., Mansour, V. H.: Platinum Compounds: a New Class of Potent Antitumor Agents. Nature, 222, 385–386 (1969)
3) Lippman, A. J., Helson, C., Krakoff, I. H.,: Clinical trials of cis-Diaminedichloroplatinum(NSC-119875). Cancer Chemother. Rep., 57, 191(1973)
4) Higby, D. J., Wallace, H. J., Holland, J.F.: cis-Diaminedichloroplatinum (NSC-119975) a phase I study, Cancer Chemother. Rep., 57, 459 (1973)
5) Loehrer, P. J., Einhorn, L. H.: Drugs Five Years Later. Cisplatin. Ann. Inter. Med., 100, 704–713 (1984)
6) Einhorn, L. H., Donohue, J.,: Vinblastine, and Bleomycin Combination Chemotherapy in Disseminated Testicular Cancer. Ann. Inter. Med., 87, 293–298 (1977)
7) Ozols, R. F., Young, R. C.: Chemotherapy of Ovarian Cancer. Semin. Oncol. 11, 251–263 (1984)
8) Wiltshaw, E.: Phase II Study of cis-Diaminedichloroplatinum (NSC-119875, CACP) in Advanced Adenocarcinoma of the Ovary. Cancer Treat. Rep., 60, 55–60 (1976)
9) Soloway, M. S.: cis-Diaminedichloroplatinum(II)(CDDP) in Advanced Bladder Cancer. J. Urol. 120, 716–719 (1978)
10) Higby, D. J., Wallace, H. J., Albert, D. Holland, J. F.: A phase I study showing responses in testicular and other tumors. Cancer, 33, 1219 (1974)
11) Clark, M. J.: Met. Complexes Cancer Chemother., 129–56 (1993)
12) Keppler, B. K., Stenzel, B., Lipponer, K. G., Vongerichten, H., Vogelin, E., Brooks, R. R.: Noble Metals and Biological Systems, CRC Press, Boca Raton, Fla., pp 323–328 (1992)
13) Fioentino, M. V., Ghiotto, C.: Platinum, the Synergistic Drug; from Clinical Evidence to Laboratory Suggestions. In Platinum and Other Metal Coordination Compounds in Cancer Chemotherapy; Nicolini, M., Ed.; Martinus Nijhoff Publishing: Boston, 415–435 (1988)
14) Wagener, D. J., Yap, S. H., Wobbes, T., Burghouts, J. T., van Dam, F. E., Hillen, H. F., Hoogendoorn, G. J., Scheerder, H., van der Vegt, S. G.: Phase II Trial of 5-Fluorouracil, Adriamycin and Cispain (FAP) in Advanced Gastric Cancer. Cancer Chemother. Pharmacol. 15, 86–87 (1985)
15) Ward, J. M., Young, D. M., Fauvie, K. A., Wopert, M. K., Davis, R., Guarno, A. M.: Comparative nephrotoxicity of platinum cancer chemo therapeutic agent, Cancer Chemother. Rep., 60, 1675(1976)
16) Von Hoff, D. D., Schilsky, R., Reichert, C. M., Reddick, R. L., Rozencweig, M., Young, R. C., Muggia, F. M.: Toxic Effects cis-Diaminedichloroplatinum(II) in Man. Cancer Treat. Rep., 63, 1527–1531 (1979)
17) Krakoff, I. H.: Nephrotoxicity of cis-Diaminedichloroplatinum(II), Cancer Treat. Rep., 63, 1523–1525 (1979)
18) Ishibiki, K., Kodair S., Abe, O., Yamamoto, K., Oochi, T., Fukaya, Y., Kimura, K., Takamatsu, K., Ootsuka, E., Sakabe, T., Nishiyama, T., Mishima, Y., Ogoshi, K., Mitomi, T.: Phase II Study with Cisplatin in Advanced Stomach and Colon Carcinoma. Jpn. J. Cancer Chemother. 16, 3185–3193 (1989)
19) Ozols, R. F.: Pharmacologic Reversal of Drug Resistance in Ovarian Cancer. Semin. Oncol. 16, 3185–3193 (1989)
20) Hong, W. S., Saijo, N., Sassaki, Y., Minato, K., Nakano, H., Nakagawa, K., Fujiwara, Y., Nomura, K.: Establishment and Characterization of Cisplatin-resistant Sublines of Human Lung Cancer lines. Int. J. Cancer 41, 462–467 (1988)
21) Inoue, K., Mukaiyama, T., Mitsui, I., Ogawa, M.: In Vitro Evaluation of Anticancer Drugs in Relation to Development of Drug Resistance in Human Tumor Clonogenic Assay. Cancer Chemother. Pharmacol. 15, 208–213 (1985)
22) Gottlieb, J. A., Drewinko, B.: Review of the current clinical status of platinum coordination complexes in cancer chemotherphy, Cancer Chemother. Rep., 59, 621 (1975)
23) Hardaker I. H., Stone, R. A., McCoy, R.: Platinum toxicity, Cancer, 34, 1030 (1974)
24) Kakoff, I. H.: Nephrotoxicity of diammine-dichloroplatinum(II), Cancer Treat. Rep., 63, 1523 (1979)
25) Jacobs, C., Kalman, S. M., Tretton, M., Weiner, M. W.: Renal handling of cis-diaminedichloroplatinum(II), Cancer Treat. Rep. 64, 1223 (1980)
26) Litterst, C. L.: Cisplatinum; A review with special reference to cellular and molecular interactions, Agents Actions, 15, 520 (1984)
27) Burchenal, J. H., Kalaber, K., Dew, K., Lokys, L.: Rationale for Developement of Platinum Analogs. Cancer Treat. Rep. 63, 1493–1498 (1979)
28) Connors, T. A., Cleare, M. J., Harrap. K. R.: Stucture-Activity Relationships of the Antitumor Platinum Coordination Complexes. Cancer Treat. Rep. 63, 1499–1502 (1979)
29) Wilkinson, R., Cox, P. J., Jone, M., Harrap, K. R.: Selection of Potential Second Generation Platinum Compouds. Biochimie. 60, 851–857 (1978)
30) Brown, D. B., Khokhar, A. R., Hacker, M. P., Lokys, L., Burchenal, J. H., Newman, R. A., McCormack, J. J., Frost, D.: Synthesis and Antitumor Activity of New Platinum Complexes. J. Med. Chem. 25, 952–956 (1982)
31) Calvert, A. R., Harland, S. J., Newell, D. R., Siddik, Z. H., Jones, A. C., McEwain, T. J., Raju, S., Wiltshaw, E., Smith, I. E., Baker, J. M., Peckman, M. J., Harrap, K. R.:Early Clinical Studies with cis-Diamine(1,1-cyclobutanedicarboxylato)Platinum(II). Cancer Chemother. Pharmacol. 9, 140–147 (1982)
32) Foster, B. J., Clagett-Carr, K., Leyland-Jones, B., Hoth, D.: Results of NCI-Sponsored Phase I Trials with Carboplatin. Cancer Treat. Rev. 12(Suppl.A), 43–49 (1985)

33) Carter, S. K., Canetta, R., Rozencweig, M.: Carboplatin: Future Directions. Cancer Treat. Rev. 12(Suppl.A), 145–152 (1985)
34) Harrap, K. R.: Preclinal Studies Identifying Carboplatin as Visible Ciaplatin Alternative. Cancer Treat. Rev. 12(Suppl.A), 21–33 (1985)
35) Canneta, R., Rozencweig, M., Carter, S. K.: Carboplatin: the Clinical Spectrum to Date. Cancer Treat. Rev. 12(Suppl.A), 125–136 (1985)
36) Gore, M., Fryatt, I., Wiltshaw, E., Dawson, T., Robbinson, B., Calvert, A.: Cisplatin/Carboplatin Cross-Resistance in Ovarian Cancer. Br. J. Cancer 60, 767–769 (1989)
37) Kikuchi, Y., Iwano, I., Miyaunci, M., Kita, T., Sugita, M. Tenjin, Y., Nagata, I.,: Possible Mechanisms of Resistance to cis-Diamine-(1,1-cyclobutanedicarboxylato)Platinum (II) of Human Ovarian Cancer Cells. Jpn. J. Cancer Res. 81, 701–706 (1990)
38) Kim, D. K., Kim, G., Gam, J., Cho, Y. B., Kim, H. T., Tai, J. H., Kim, K. H., Hong, W. S., Park, J. G.: Synthesis and Antitumor Activity of a Series of [2-substituted-4,5-bis(aminomethyl)-1,3-dioxolane] Pt(II) Complexes. J. Med. Chem. 37(10), 1471–85 (1994)
39) Kim, D. K., Kim, H. T., Cho, Y. B., Tai, J. H., Ahn, J. S., Kim, K. H., Hong, W. S.,: Antitumor Activity of cis-malonato[(4R,5R)-4,5-bis(aminomethyl)-2-isopropyl-1,3-dioxolane]platinum(II), a new platinum analogue, as an anticancer agent. Cancer Chemother. Pharmacol 44(5), 441–445 (1995)
40) Kim, D. K., Kim, H. T., Tai, J. H., Cho, Y. B., Kim, K. H., Park, J. G. Hong, W. S.: Pharmacokinetics and Antitumor Activity of a new platinum compound, cis-malonato[(4R,5R)-4,5-bis(aminomethyl)-2-isopropyl-1,3-dioxolane]platinum(II)(SKI 2053R), determined by ex vivo pharmacodynamics. Cancer Chemother. Pharmacol. 37(1–2), 1–6 (1995)
41) Kim, N. K., Bang, Y. J., Heo, D. S., Kim, T. Y., Lee, J. A., Park, Y. I., Shin, S. G., Cho, Y. B., Kim, K. H., Kim, D. K.: A phase I clinical and pharmacokinetic study of SKI 2053R, a new platinum analog in patients with malignanies. Proc. Amer. Soc. Clin. Oncol. 14, Abst 1556 (1995)
42) Weiss, R. B., Christian, M.: Drugs, 46, 360–377 (1993)
43 Kelland, L. R., co-workers, Cancer Res. 53, 2581–2586 (1993)
44) Kelland, L. R., McKeage, M. J.: New platinum agents. Acomparison in ovarian cancer. Drugs Aging, August 5(2), 85–95 (1994)
45) Nowatari, H., Kuroda, Y., Hayami, H., Okamoto, K., Ekimoto, H., Takahashi, K: Synthesis and Antitumor Activity of Alkyl-1,4-butanediamine Pt(II) Complexes Having Seven-membered Ring Structure. Chem. Pharm. Bull. 37, 2406–2409 (1989)
46) Yamaue, H., Tanimura, H., Tani, M., Iwahashi, M., Tsunoda, T.,: In Vitro Antitumor Activity of a New Platinum Analogue, NK-121 against Fresh Human Tumor Cells and Established Tumor Cell Lines by Succinate Dehydogenase Inhibition Test. Chemotherapy (Tokyo) 38, 780–789 (1990)
47) Morikawa, K., Honda, M., Endoh, K., Matsumoto, T., Akamatsu, K., Mitsui, H., Koizumi, M.: Synthesis, Antitumor Activity and Nephrotoxicity of the Optical Isomers of 2-Aminomethylpyrrolidine (1,1-cyclobutanedicarboxylato)platinum(II). J. Pharm. Sci. 80, 837–842 (1991)
48) Matsumoto, T., Endoh, K., Akamatsu, K., Kamisango, K., Mitsui, H., Koizumi, M. Morikawa, K., Koizumi, M., Matsuno, T.: Comparison of the Antitumor Effect and Nephrotoxicity-Inducing Activities of Two New Platinum Complexes, (−)-(R)-2-(aminomethyl)pyrrolidine (1,1-cyclobutanedicarboxylato)platinum(II)Monohydrate, and Its Enantiomeric Isomer. Br. J. Cancer 84, 41–46 (1991)
49) Kamisango, K., Matsumoto, T., Akamatsu, K., Morikawa, K., Tashiro, T., Koizumi, K.: Antitumor Activity and Cellular Accumulation of a New Platinum Complex, (−)-(R)-2-(aminomethyl)pyrrolidine(1,1-cyclobutanedicaroxylato)platinum(II) Monohydrate, in Cisplatin-sensitive and -resistant Murine P388 Luekemia Cells. Jpn. J. Cancer Res. 83, 304–311 (1992)
50) Totani, T., Aono, K., Komura, M., Adachi, Y.: Synthesis of (Glycolato-O,O')diamineplatinum(II) and Its Related Complexes. Chem. Lett. 26, 393–396 (1990)
51) Fukuda, M., Shinkai, T., Eguchi, K., Sasaki, Y., Tamura, T., Ohe, Y., Kojima, A., Oshita, F., Hara, K., Saijo, N.: Phase II Study of (Glycolato-O,O')diamineplatinum(II), a Novel Platinum Complex, in the Treatment of Non-Small-Cell Lung Cancer. Cancer Chemother. Pharmacol. 26, 393–396 (1990)
52) Mathe, G., Kidani, Y., Noji, M., Maral, C., Bourut, C., Chenu, E.: Antitumor activity of 1-OHP in mice. Cancer Lett. 27, 135 (1985)
53) Tashiro, T., Kawada, Y., Sakura, Y., Kidani, Y.,: Antitumor activity of a new Platinum Compex, oxalato(trans-1-1,2-diaminocyclohexane)platinum(II); new experimental data. Biomed. & Pharmacother. 43, 251 (1989)
54) Anderson W. K., Quagliato, D. A., Haugwitz, R. D., Narayanan, V. L., Wolpert-DeFilippes, M. K.: Synthesis, Physical Properties, and Antitumor activity of Tetraplatin and Related Tetrachloroplatinum(IV) Stereoisomers of 1,2-diaminocylohexane. Cancer Treat. Rep. 70, 997–1002 (1986)
55) McPherson, R. A., Roh, J. K., Komanduri, K., Mhatre. R., Wooley, P. V., Rahman, A.: Toxicological Evaluation of Tetraplatin(NSC363812) in Comparision to CDDP. Proc. Am. Assoc. Cancer Res. 27, Abst. 1153 (1986)
56) Rahman, A. Roh, J. K., Wolpert-DeFilippes, M. K., Goldin, A., Venditti, J. M., Wooley, P. V.: Therapeutic and Pharmacological studies of tetrachloro-[(d,1-trans)-1,2-diaminocyclohexane)platinum(IV) (tetraplatin), a new Platinum Anlaog. Cancer Res., 48, 1745 (1988)
57) Bramwell, V. H. C., Crowther, D., O'Malley, S., Swindell, R., Johnson, R., Cooper, E. H., Thatcher, N., Howell, A.: Activity of JMG(CHIP) in advanced ovarian cancer; a phase I–II trial. Cancer Treat. Rep., 69, 409 (1985)
58) Hortobagyi, G., Holmes, F., Frye, D., Hug, V., Fraschini, G.: A phase II Study of CHIP in metastatic breast cancer (MBC). Proc. Am. Assoc. Cancer Res., 28, 788 (1987)
59) Hrubisko, M., Kysela, B., Kuliffay, P.: Growth, Flow cytometric, and karyological characterization of L1210 cell sublines resistant to various Pt derivatives. Neoplasma, 36(4), 401–410 (1989)
60) Bierbach, U., Hambley, T. W., Farrell, N.: Inorg. Chem. 37, 708 (1998)
61) Bierbach, U., Roberts, J. D., Farrell, N.: Modification of Platinum(II) Antitumor Complexes with Sulfur Ligands. 2.Reactivity and Nucleotide Binding Properties of Cationic Complexes of the Types [PtCl(diamine)(L)]$NO_3$ and {[PtCl(diamine)}$_2$(L-L)]$(NO_3)_2$ (L=Monofunctional Thiourea Deivative; L-L=Bifunctional Thiourea Derivative) in Relation to Their Cytotoxicity, Iorg. Chem. 37, 717–723, (1998)
62) Quinga, A. G., Perez, J. M., Lopez-Solera, I., Masaguer, J. R., Luque, A. Roman, P., Edwards, A., Alonso, C., 63) Navarro-Ranninger, C.: Novel Tetranuclear Orthometalated Complexes of Pd(II) and Pt(II) Derived from p-Isopropylbenzaldehyde Thiosemicarbazone with Cytotoxic Activity in cis-DDP Resistant Tumor Cill Lines. Interaction of These Complexes with DNA, J. Med. Chem., 41, 1399–1408 (1998)
63) Khokhar, A. R., Deung, Y., Kido, Y., Siddik, Z. H.: Preparation, Characterization, and Antitumor Activity of New Ethylenediamine Platinum(IV) Complexes Containing Mixed Carboxylate Ligands, J. Inorg. Biochem. 50, 79–87(1993)
64) Shamsuddin, S., Takahashi, Ikuo, Siddik, Z. H., Khokha, A. R.: Synthesis, Characterization, and Antitumor Activity of a Series of Novel Cisplatin Analogs with cis-1,4-Diaminocyclohexane as Nonleaving Amine, Group, J. Inorg. Biochem. 61, 291–301 (1996)
65) Shamsuddin, S., Hal, J. W., Stark, J. L., Whitmire, K. H., Khokhar, A. R.: Synthesis and Characterization of Novel Axial Dichloroplatinum(IV) Cisplatin Analogues; Crystal Structure of an Axial Dichloro Complex [Pt(cis-1,4-DACH)(trans-$Cl_2$)(CBDCA)].½MeOH, Inorg. Chem. 36, 5969–5971 (1997)
66) Munchausen L. L.: The chemical and biological effects of cis-dichlorodiamine platinum(II), an antitumor agent, on DNA. Proc. Natl. Acad. Sci. USA, 71, 4519 (1974)
67) Pascoe, J. M., Roberts, J. J.: Interaction between mammalian cell DNA and inorganic platinum(II) compounds; DNA intrastrand crosslinking and cytotoxic properties of platinum(II) compounds, Biochem. Pharmacol., 23, 1345 (1974)
68) Harder, H. C., Rosenberg, B.: Inhibitory effects of antitomor platinum compounds on DNA, RNA and protein synthases in mammalian cells in vitro, Int. J. Cancer, 6, 207 (1970)
69) Sherman, S. E., Lippard, S. J.: Structural Aspects of Platinum Anticancer Drug Interactions with DNA, Chem. Rev., 87, 1153–1181 (1987)
70) Stone, P. J., Kelman, A. D., Sinex, F. M.: Specific binding of antitumor drug cis-Pt$(NH_3)_2Cl_2$ to DNA rich in guanine and cytosine, Nature, 251, 736 (1974)
71) Tullius, T. D., Lippard, S. J.: cis-Diaminodichloroplatinum(II) binds in unique manner to oligo(dG).oligo(dC) sequences in DNA—a new assay using exonuclease III, J. Am. Chem. Soc., 103, 4620 (1981)
72) Royer-Pokora, B., Gordon, L. K., Hoseltine, W. A.: Use of exonuclease III to determine the site of stable lesion in defined sequences of DNA; the cyclobutane pyrimidine dimer and cis and trans-dichlorodiammine platinum(II) examples, Nucleic Acids Res., 9, 4595 (1981)
73) Caradonna, J. P., Lippard, S. J.: Inorg. Chem. 27, 1454 (1988)
74) Reily, M. D., Marzilli, L. G.: Anticancer Pt drug adduct with AMP; novel direct 1H and 195Pt NMR evidence for slowly interconverting "head to tail" rotamers. Potential role of amine ligand bulk and NH groups in guanine selectivity and anticancer activity, J. Am. Chem. Soc., 108, 6785 (1986)
75) Lippard, S. J. Hoeschele, J. D.: Binding of cis- and trans-dichlorodiammine platinum(II) to the nucleosome core, Proc. Natl. Acad. Sci. USA, 76, 6091 (1979)
76) Laurent, G., Erickson, L. C., Shakey, N. A., Kohn, K. W.,: DNA crosslinking and cytotoxicity induced by cis-diamminedichloro platinum(II) in human normal and tumor cell lines, Cancer Res., 41, 3347 (1981)
77) Zwedlling, L. A., Anderson, T., Kohn, K. W.: DNA-protein and DNA intrastrand crosslinking by cis and trans-dichlorodiammine platinnum(II) in L1210 mouse leukemia cells and relation to cytotoxicity, Cancer Res., 39, 365 (1979)
78) Erikson, L. C., Zwelling, L. A., Ducore, J. M., Shakey, N. A., Kohn, K. W.: Differential cytotoxicity DNA intrastrand crosslinking in normal and transformed human fibroblasts treated with cis-diamminedichloro platinum (II), Cancer Res., 41, 2791 (1981)
79) Pera, M. F., Rawlings, J., Roberts, J. J.: The role of DNA repair in the recovery of human cells from cisplatin toxicity, Chem.-Biol. Interact, 37, 245 (1981)
80) Roberts, J. J., Friedlos, F.: Quantitative aspects of the formation and loss of DNA interstrand crosslinks in chinese hamster cells following treatment with cis-diaminedichloroplatinum(II)(cisplatin), Biochim Biophys. Acta, 655, 146 (1981)
81) Rosenberg, B.: Platinum complex-DNA interactions and anticancer activity, Biochimie, 60, 859 (1978)
82) Macquet, J. P., Butour, J. L.: DNA-platinum interactions; Fluorescence studies and DNA saturation with cis-diamine Pt(II) chloride, Ibid, 60, 901 (1978)
83) Goodgame, D. M. L., Jeeves, I., Phillips, F. L., Skapski, A. C.: Possible mode of action of antitumor platinum drugs. X-ray evidence for cis binding by platinum of two inosine 5'-monophosphate molecules via the N(7) positions, Biochim. Biophys. Acta, 378, 153 (1975)
84) Pinto, A. L., Lippard, S. J.: Binding of the antitumor drug cis-diaminedichloroplatinum(II)(cisplatin) to DNA,: Biochim. Biophys. Acta, 780, 167 (1985)
85) Eastman, A.: Biochemistry, 25, 3912 (1988)
86) Pinto, A. L., Lippard, S. J.: SEquence-dependent termination of in vitro DNA synthesis by cis- and trans-diaminedichloroplatinum(II), Proc. Natl. Acad. Sci. USA, 82, 4616 (1985)
87) Sherman, S. E., Lippard, S. J.: Structural aspects of platinum anticancer drug interactions with DNA, Chem. Rev., 87, 1153 (1987)
88) Beck, D. J., Brubaker, R. R.: Effect of cis-platinum(II) diaminodichloride on wild type and deoxyribonucleic acid repair-deficient mutants of *Escherichia coli*, J. Bacteriol, 116, 1247 (1973)
89) Brouwer, J., Van de Putte, P., Fichtinger-Schepman, A. M. J., Reedijk, J.: Base-pair substitution hotspots in GAG and GCG nucleotide sequences in *Escherichia coli* K-12 induced by cis-diaminedichloroplatinum(II), Proc. Natl. Acad. Sci. USA, 78, 7010 (1981)
90) Plooy, A. C. M., Van Dijk, M., Berends, F., Lohman, P. H. M.: Formation and repair of DNA interstrand crosslinks in relation to cytotoxicity and unscheduled DNA synthesis induced in control and mutant human cells treated with cis-diaminedichloroplatinum(II), Cancer Res. 45, 4178 (1985)
91) Lim, M. C., Martin, R. B.: The nature of cis amine Pd(II) and antitumor cis amine Pt(II) complexes in aqueous solutions, J. Inorg. Nucl. Chem., 38, 1911 (1976)
92) Johnson, N. P., Hoeschele, J. D., Rahn, R. O.: Kinetic analysis of the in vitro binding of radioactive cis- and trans-dichlorodiamineplatinum(II) to DNA, Chem.-Biol. Interact., 30, 151 (1980)
93) Ushay, H. M., Tullius, T. D., Lippard, S. J.: Inhibition of BamHI cleavage and unwinding of pBR 322 deoxyribonucleic acid by the antitumor drug cis-dichlorodiamineplatinum(II), Biochemistry, 20, 3744 (1981)
94) Alaoui, S., Lawry, J., Griffin, M.: The cell cycle and induction of apoptosis in a hamster fibrosarcoma cell line treated with anti-cancer drugs: its importance to solid tumour chemotherapy, Neurooncol., 31(1–2), 196–207 (1997)

95) Dimanche-Boitrel, M. T., Micheau, O., Hammann, A., Haugg, M., Eymin, B., Chauffert, B., Solary, E.: Contribution of the cyclin-dependent kinase inibitor p27KIP1 to the confluence-dependent resistance of HT29 human colon carcinoma cells, Int. J. Cancer, August 31;77(5), 796–802 (1998)

96) Ferrandina, G., Melichar, B., Loercher, A., Verschaegen, C. F., Kudelka, A. P., Edwards, C. L., Scambia, G., Kavanagh, J. J., Abbruzzese, J. L., Freedman, R. S.: Growth inhibitory effects of sodium phenylacetate (NSC 3039) on ovarian cacinoma cells in vitro, Cancer Res., 57(19), 4309–15 (997)

97) Borner, M. M., Joncourt, F., Hotz, M. A: Simiarity of apoptosis induction by 2-chlorodeoxyadenosine and cis-platinin human mononuclear blood cells, Br. J. Cancer, 76(11), 1448–54 (1997)

98) Light, B. W., Yu, W. D., McElwain, M. C., Russell, D. M., Trump, D. L., Johnson, C. S.: Potentiation of cisplatin antitumor activity using a vitamin D analogue in amurine squamous cell carcinoma model system, Cancer Res., September 1;57(17), 3759–64, (1997)

99) Iida, T., Yoshida, N., Kuramoto, H., Shimoda, T., Hamano, M., Hata, H., Yonamine, K., Hayashi, K.: Establishment of a new human ovarian serous cystadenocarcinoma cell line (IM), and influence on cell proliferations by cisplatin with or without hyperthermia, Hum Cell, December;9(4), 345–52 (1996)

100) Epp, R. A., Justice, W. M., Garcia, F. U., McGregor, D. H., Giri, S. P., Kimler, B. F.: Retrospective DNA ploidy analysis by image and flow cytometry in head and neck cancer, Laryngoscope, October;106(10), 1306–13 (1996)

101) Stone, S., Dayananth, P., Kumb, A.: Reversible, p16-mediated cell cycle arrest as protection from chemotherapy. Cancer Res., July 15;56(14), 3199–202 (1996)

102) Davol, P. A., Goulette, F. A., Frackelton A. R., Darnowski, J. W.: Modulation of p53 expression by human recombinant interferon-alpha2a correlates with abrogation of cisplatin reistance in a human melanoma cell line, Cancer Res., June 1;56(11), 2522–6 (1996)

103) Otto, A. M., Paddenberg, R., Schubert S., Mannherz, H. G.: Cell-cycle arrest, micronucleus formation, and cell death in growth inhibition of MCF-7 breast cancer cells by tamoxifen and cisplatin, J. Cancer Res. Clin. Oncol., 122(10), 603–12 (1996)

104) Garrido, C., Chauffert B., Pinard, D., Tibaut, F., Genne, P., Assem, M., Dimanche-Boitrel, M. T.: Circumvention of confluence-dependent resistance in a human multi-drug-resistant colon-cancer cell line. Int. J. Cancer, June 9;61(6), 873–9 (1996)

105) Perras, J. P., Ramos, R., Sevin, B. U.: Demonstration of an S phase population of cells without DNA synthesis generated by cisplatin and pentoxifylline, Cytometry, 14(4), 441-8 (1993)

106) Tamura, J., Tanaka, J., Fujita, K., Yoshida, M., Kasamatsu, T., Arii, S., Tobe, T.: Effect of anticancer agents on cell cycle of regenerating hepatocytes in rats, J. Surg. Res., September;53(3), 218–26 (1992)

107) Azumi, Y., Konishi, E., Urata, Y., Itoi, H., Yamaguchi, N., Kubo, H., Horii, A., Yamagishi, H., Ashihara, T., Oka, T.: Analysis of cell proliferation kinetics and the effects of cisplatin on the cell cycle of human gastric cancer cells by autostage cytofluorometry, Gan To Kagaku Ryoho, July;19(7), 987–92 (1992)

108) Kubbies, M., Goller, B., Schettes, B., Bartosek, I., Albert, W.: Glutathione restores normal cell activation and cell cycle progression in cis-platinum treated human lymphocytes, Br. J. Cancer, November;64(5), 843–9 (1991)

109) Shinomiya, N., Katsura, Y., Tsugita, M., Noritake, M., Tsuru, S.: Analysis of tumor cell growth and effects of antitumor drugs on cell cycle regulation by flow cytometry, Gan To Kagaku Ryoho, September;18(12), 2109–15 (1991)

110) Poot, M., Schuster, A., Hoehn, H.: Cytostatic synergism between bromodeoxyuridine, bleomycin, cisplatin and chlorambucil demonstrated by a sensitive cell kinetic assay, Biochem. Pharmacol. June 15;41(12), 1903–1909 (1991)

111) Di Martino, D., Avignolo, C., Marsano, B., Di Vinci, A., Cara, A., Giaretti, W., Tonini, G. P.: Neurite outgrowth and cell cycle kinetic changes induced by cis-diamminedichloroplatinum II and retinoic acid in a human neuroblastoma cell line, Cancer Lett., July 16;52 (2), 101–106 (1990)

112) Rauko, P., Sedlak, J., Duraj, J., Szekeres, M. F., Novotny, L.: Pentoxifylline stimulates drug-induced apoptosis in leukemic cells, Neoplasma, 45(5), 296–300 (1998)

113) Ormerod, M. G., O'Neill, C., Robertson, D., Kelland, L. R., Harrap, K. R.: cis-Diamminedichloroplatinum(II)-induced cell death through apoptosis in sensitive and resistant human ovarian carcinoma cell lines, Cancer Chemother. Pharmacol., 37(5), 463–71 (1996)

114) Engelke, K. J., Hacker, M. P.: A non-characteristic response of L1210 cells to lovastatin, Biochem. Biophys. Res. Commun. August 30;203(1), 400–407 (1994)

115) Kobayashi, E., Okamoto, A., Asada, M., Okabe, M., Nagamura, S., Asai, A., Saito, H., Gomi, K., Hirata, T.: Characteristics of anti-tumor activity of KW-2189, a novel water-soluble derivative of duocarmycin, against murine and human tumors, Cancer Res., May 1;54(9), 2404–2410 (1994)

116) Ormerod, M. G., Orr, R. M., Peacock, J. H.: The role of apoptosis in cell killing by cisplatin: a flow cytometric study, Br. J. Cancer, January;69(1), 93–100 (1994)

117) Sorenson, C. M., Barry, M. A., Eastman, A.: Analysis of events associated with cell cycle arrest at G2 phase and cell death induced by cisplatin, J. Natl. Cancer Inst., May 2;82(9), 749–755 (1990)

118) Sorenson, C. M., Eastman, A.: Infuence of cis-diamminedichloro platinum(II) on DNA synthesis and cell cycle progression in excision repir proficient and deficient Chinese hamster ovary cells, Cancer Res., December 1;48(23), 6703–7 (1988)

119) Sorenson, C. M., Eastman, A: Medrnnism of cis-diamminedichloro platium(II)-induced cytotoxicity: role d G2 arrest and DNA double-strand breaks, Cancer Res., August15;48(16), 4484–4488(1988)

120) Ormerod, M. G., Orr, R. M., O'Neill, C. F., Chawalinski, T., Titley, J. C., Kelland, L. R. Harrap, K. R.: The cytotoxic action of four ammine/amine platinum(IV) dicarboxylates: a flow cytometric study, Br. J. Cancer, December;74(12), 1935–1943 (1996)

121) Lee, K. I., Tashiro, T., Noji, M.: Platinum and Palladiun Complexes Contaning Ethlenediamine Derivatives as Carner Ligands and Their Antitumor Activity. Chem. Pharm. Bull., 42(3) 702–708 (1994)

122) Carmichael, J., DeGraff, W. G., Gazdar, A. F., Minna, J. D., Mitchell, J. B.: Evaluation of a Tetrazolium-based Semniautomated Colorimetric Assay; Assessment of Chemosensitivity Testing, Cancer Res., 47, 936–942 (1987)

123) Scudiero, D. A., Shoemaker, R. H., Paull, K. D. Monks, A., Tierney, S., Nofziger, T. H., Currens, M. J., Seniff, D., Boyd, M. R.: Evaluation of a Soluble Tetrazolium/

123) Formazan Assay for Cell Growth and Drug Sensitivity in Culture Using Human and Other Tumor Cell Lines, Cancer Res., 48, 4827–4833 (1988)

124) Vistica, D. T., Skehan, P., Scudiero, D. A., Monks, A., Pittman, A., Boyd, M. R.: Tetrazolium-based Assys for Cellular Viability: A Critical Examination of Selected Parameters Affecting Formazan Production, Cancer Res., 51, 2515–2520 (1991)

125) Whang, K. J. Lee, K. I., Kwon, Y. E.: Design of new Platinum complexes and thier antitumor activity, J. Pharm. Sci. Sookmyung W. Univ. 12, 31–39 (1996)

126) Kensler, G. I., Sugiura, K., Young, N. F. Halter, C. R. Rhodas, C. P.: Science, 93, 308 (1941)

127) Thurnham, D. I., Zheng, S. F., Munoz, N., Crespi, M., Grassi, A., Hambridge, M., Chai. T. F.: Comparison of riboflavin, Vitamine A and zinc status of Chinese populations ations at high and low risk for oesophageal cancer. Nutrition and Cancer 7, 131–143 (1985)

128) Bespalov, V. G., Troian, D. N., Petrov, A. S., Aleksandrov, V. A.: The effect of riboflavin, molybdenum, selenium and zinc on the development of induced tumors of esophagus and forestomach in rats, Vopr. Onkol. 36(5), 559–563 (1990)

129) Pangekar, J., Krishnaswamy, Jagadeesan, V.: Effects of Riboflavin deficiency and Riboflavin administration on Carcinogen-DNA binding, Fd. Chem. Toxic., 31(10), 745–750 (1993)

130) Lin, P., Zhang, J., Rong, Z., Han, R., Xu, S., Gao, R. Ding, Z., Wang, J., Feng, H., Cao, S.: Studies on medicamentous inhibitory theraphy for esophageal precancerous lesions 3- and 5-year inhibitory effects of antitumor-B, retinamide and riboflavin, Proc. Chin. Acad. Med. Sci. Peking Union Med. Coll., 5(3),121–129 (1990)

131) Suzi, K., Noji, M., Tashiro, T. Kidani, Y.: Synthesis and Antitumor Activity of Riboflavin and Flavin Mononucleotide Pt(II) Complexes, Chem. Pharm. Bull. 36(5), 1895–1898 (1988)

132) Granzow, C. Kopun, M., Krober, T.: Riboflavin-mediated plotosensitization of Vinca alkaloids distorts drug sensitivity assays, Cancer Res., 55(21), 4837–4843 (1995)

133) Rose, W. C., Schurig, J. E., Huftalen, J. B., Bradner, W. T.: Antitmor Activity and Toxicity of Cisplatin Analogs, Cancer Treat. Rep., 66, 135–146 (1982)

134) Ban, M., Hettich, D., Huguet, N.: Nephrotoxicity mechanism of cis-platinum (II) diamine dichloride in mice, Toxicol. Lett. April;71(2), 161–8 (1994)

135) Reeves, P. G., Noordewier, B., Saari, J. T.: Effect of copper deficiency and cis-diamminedichloroplatinum(II) treatment on the activities of renal microvillar enzymes in rats, J. Trace Elem. Electrolytes Health Dis. March;4(1), 11–9 (1990)

136) Suzki, M., Ohwada, M., Sekiguchi, I., Tamada, T.: Histopathological study regarding the protective effect of elastase on cis-platinum-induced renal toxicity, Nippon Gan Chiryo Gakkai Shi., May 20;24(5), 941–7 (1989)

137) Jones, T. W., Chorpa, S., Kaufman, J. S., Flamenbaum, W., Trump, B. F.: Cis-diamminedichloroplatinum (II)-induced acute renal failure in the rat: enzyme histochemical studies, Toxicol. Pathol., 13(4), 296–305 (1985)

138) Nakamura, M., Imaoka, M., Tanaka, E., Misawa, S., Funae, Y.: cis-Diamminedichloroplatinum induces peroxisomes as well as CYP4A1 in rat kidney. Res. Commun Mol. Pathol. Pharmacol. January;99(1), 23–32 (1998)

139) Leibbrandt, M. E., Wolfgang, G. H., Metz, A. L., Ozobia, A. A, Haskins, J. R.: Critical subcellular targets of cisplatin and related platinun analogs in rat renal proximal tubule cells, Kidney Int. September;48(3), 761–70 (1995)

140) Yasumasu, T., Ueda, T., Uozumi, J., Mihara, Y., Koikawa, Y., Kumazawa, J.: Ultrastructural alterations and DNA synthesis of renal cell nuclei following cisplatin or carboplatin injection in rats, J. Pharm. Pharmacol., November;44(11), 885–7 (1992)

141) Singh, G.: A possible cellular mechanism of cisplatin-induced nephrotoxicity, Toxicology, September;58(1), 71–80 (1989)

142) Roh, J. K., Chung, H. C., Koh, E. H., Lee, W. Y., Hahn, J. S., Kim, B. S.: In vitro cytotoxicity of various anticancer drugs to short-term cultured gastric adenocarcinoma cell line, J. of Korean Cancer Association, 23, 3 (1991)

143) Lee, K. H., Kim, C. H.: Comparision of In Vitro bioassay for the screening of antitumor substances J. of Korean Cancer Association, 27, 5 (1995)

144) Gomori, G.: Distribution of acid phosphatase in the tissue under normal and pathological conditioms, Arch. Pathol., 32, 189–199 (1941)

145) Anderson, W. K., Qualiato, D. A, Haugwitz, R. D., Narayanan, V. L, Wolpert-DeFili ppse, M. K.,: Synthesis, physical propperties and antitumor activity of tetraplatin and realated tetrachloroplutinum(IV) streoisomers of 1,2-aminocyclohexane, Cancer Treat. Rep., 70, 997 (1986)

146) Rahman, A., Roh, J. K., Wolpert-DeFilippse, M. K., Goldin, A., Venditti, J. M., Wooley, P. V.: Therapeutic and pharmacological studies of tetrachloro(d,1-tras)1,2-diaminocyclohexaneplatinum(IV) (tetraplatin), a new platinum analog., Cancer Res., 48 1745 (1988)

147) Razaka, H., Salles, B., Villani, G., Johnson, N. P.: Toxicity, mutagenicity and induction of recA protein in *Escherichia coli* treated with cis-diamine dichloroplatinum (II) and cis-diamine tetrachloroplatinum(V), Chem.-Biol. Interact, 60, 207(1986)

148) van der Veer, J. L., Peters, A. R., Reedijk, J.: Reaction products form platinum(IV) amine complouds and 5'-GMP are mainly bis(5'-GMP) platinum(II) amine adducts, J. Inorg. Biochem., 26, 137 (1986)

What is claimed is:

1. An anti-cancer compound represented by the following Chemical Formula 3,

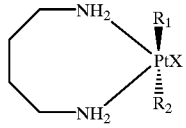

<Chemical Formula 3> wherein,

X is $Cl_2$,

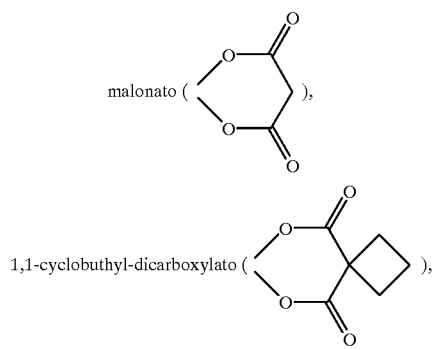

-continued oxalato ( 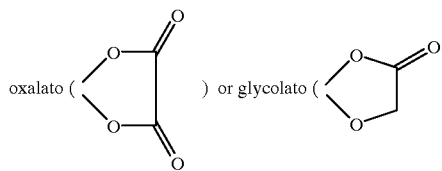 ) or glycolato ( );

and $R_1$ and $R_2$ are independently —OH, —Cl, —OCOCH$_3$, —OCOCF$_3$, —OCO(CH$_2$)$_n$CH$_3$ or —OCO(CH$_2$)$_n$CF$_3$ (n is an integer of 1 to 4).

2. An anti-cancer compound according to the claim 1, which is selected from the group consisting of the following Chemical Formulas 4 to 9, <Chemical Formula 4>

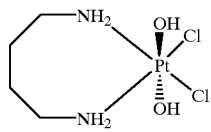

trans, cis-dihydroxo, dichloro-1,4-butanediamine Pt(IV) complex

<Chemical Formula 5>

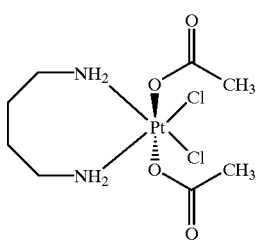

trans, cis-diacetato, dichloro-1,4-butanediamine Pt(IV) complex

<Chemical Formula 6>

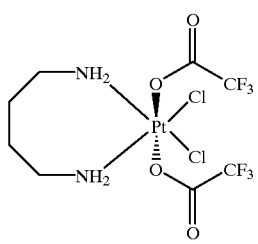

trans, cis-ditrifluoro acetato, dichloro-1,4-butanediamine Pt(IV) complex

<Chemical Formula 7>

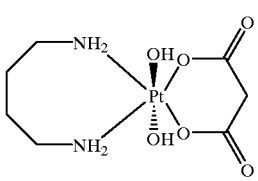

trans-dihydroxo, malonato-1,4-butanediamine PT(IV) complex

<Chemical Formula 8>

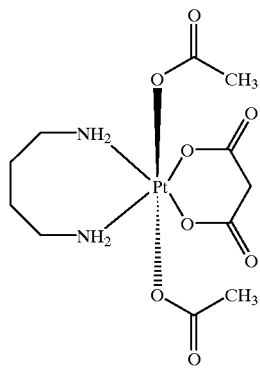

trans-diacetato, malonato-1,4-butanediamine Pt(IV) complex

<Chemical Formula 9>

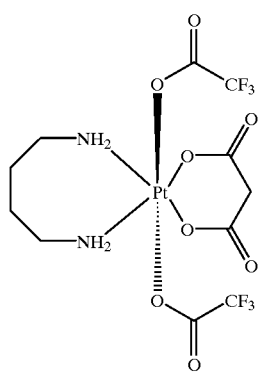

trans-ditrifluoroacetato, malonato-1,4-butanediamine Pt (IV) complex.

3. A pharmaceutical composition comprising the compound represented by the following Chemical Formula 3, <Chemical Formula 3>

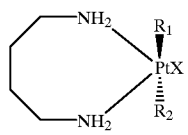

wherein,

X is Cl$_2$, malonato ( 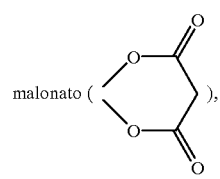 ), 1,1-cyclobuthyl-dicarboxylato ( 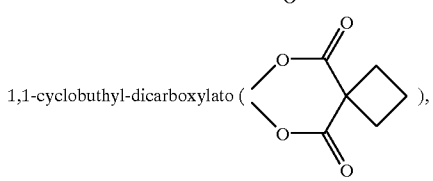 ), oxalato ( 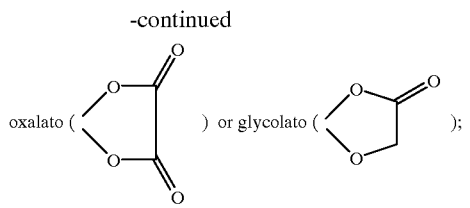 ) or glycolato ( );

and R$_1$ and R$_2$ are independently —OH, —Cl, —OCOCH$_3$, —OCOCF$_3$, —OCO(CH$_2$)$_n$CH$_3$ or —OCO(CH$_2$)$_n$CF$_3$ (n is an integer of 1 to 4).

4. A pharmaceutical composition according to claim 3, which is used as an anti-cancer agent.

5. A pharmaceutical composition according to claim 3, said composition further comprising pharmaceutically acceptable carrier.

6. A pharmaceutical composition according to claim 3, which can be orally adminstered.

7. A method for synthesizing the compound represented by the following Formula 4, which comprises the steps of:
 (a) preparing dichloro-1,4butanediamine Pt (II) complex; and
 (b) adding 30% H$_2$O$_2$ to the dichloro-1,4butanediamine Pt (II) complex, <Chemical Formula 4>

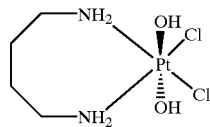

trans, cis-dihydroxo, dichloro-1,4-butanediamine Pt(IV) complex.

8. A method for synthesizing the compound represented by the following Formula 5, which comprises the steps of:
 (a) preparing trans, cis-dihydroxo, dichloro-1,4-butanediamine Pt(II) complex; and
 (b) having acetic anhydride and the dichloro-1,4 butanediamine Pt (II) complex reacted in CH$_2$Cl$_2$, to obtain the compound represented by the following Chemical Formula 5, <Chemical Formula 5>

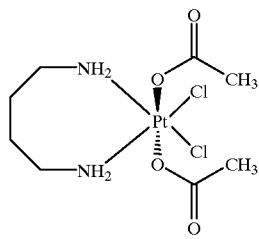

trans, cis-diacetato, dichloro-1,4-butanediamine Pt(IV) complex.

9. A method for synthesizing the compound represented by the following Chemical Formula 6, which comprises the steps of:
 (a) preparing trans, cis-dihydroxo, dichloro-1,4 butanediamine Pt (II) complex; and
 (b) having trifluroacetic anhydride and the dichloro-1,4 butanediamine Pt (II) complex reacted in CH$_2$Cl$_2$ to obtain the compound represented by the following Chemical Formula 6, <Chemical Formula 6>

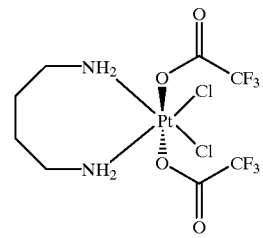

trans, cis-ditrifluoro acetato, dichloro-1,4-butanediamine Pt(IV) complex.

10. A method for synthesizing the compound represented by the following Chemical Formula 7, which comprises the steps of:
 (a) preparing malonato-1,4-butanediamine Pt (II) complex; and
 (b) adding an excessive amount of 30% H$_2$O$_2$ to the malonato-1,4-butanediamine Pt (II) complex, to obtain the compound represented by the following Chemical Formula 7, <Chemical Formula 7>

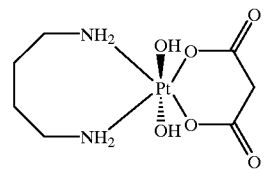

trans-dihydroxo, malonato-1,4-butanediamine Pt(IV) complex.

11. A method according to claim 10, wherein said (a) step comprising
 (i) having cis-diiodo-1,4-butanediamine Pt(II) complex and disilver malonate salt reacted; and
 (ii) after removing AgI precipitate from the resultant solution, concentrating the resultant to obtain malonato-1,4-butanediamine Pt(II) complex.

12. A method according to claim 10, wherein said (b) step is performed at room timperature.

13. A method for synthesizing the compound represented by the following Chemical Formula 8, which comprises the steps of:
 (a) preparing trans-dihydroxo, malonato-1,4-butanediamine Pt (II) complex; and
 (b) adding an excessive amount of 30% acetic anhydride to the trans-dihydroxo, malonato-1,4-butanediamine Pt (II) complex in CH$_2$Cl$_2$, to obtain the compound represented by the following Chemical Formula 8,

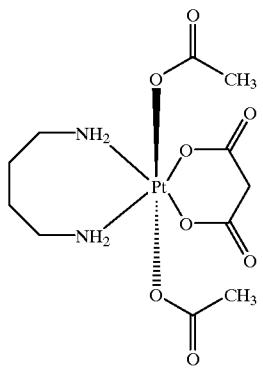

trans-diacetato, malonato-1,4-butanediamine Pt(IV) complex.

14. A method for synthesizing the compound represented by the following Chemical Formula 9, which comprises the steps of:

(a) preparing trans-dihydroxo, malonato-1,4-butanediamine Pt (II) complex; and (b) adding an excessive amount of trifluoroacetic anhydride to the trans-dihydroxo, malonato-1,4-butanediamine Pt (II) complex in $CH_2Cl_2$ solvent, to obtain the compound represented by the following Chemical Formula 9, <Chemical Formula 9>

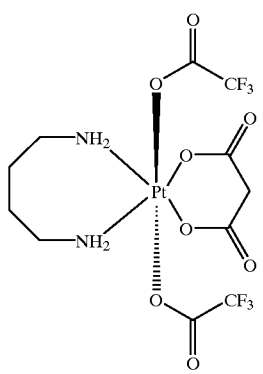

trans-ditrifluoroacetato, malonato-1,4-butanediamine Pt(IV) complex.

15. An intermediate material for synthesizing the compound represented by the following Chemical Formula 3, which is selected from the group consisting of Chemical Formulas 4 and 7, <Chemical Formula 3>

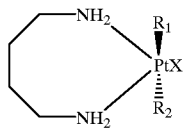

wherein,

X is $Cl_2$,

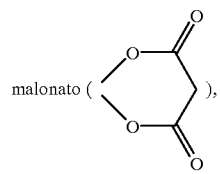

malonato ( ),

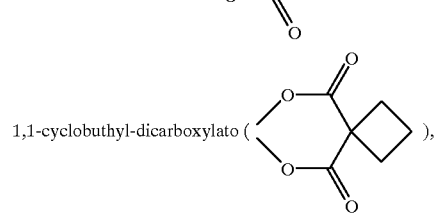

1,1-cyclobuthyl-dicarboxylato ( ),

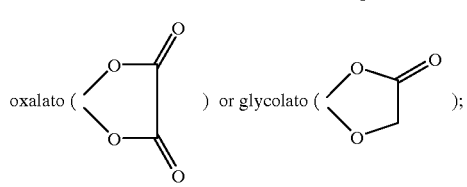

oxalato ( ) or glycolato ( );

and $R_1$ and $R_2$ are independently —OH, —Cl, —OCOCH$_3$, —OCOCF$_3$, —OCO(CH$_2$)$_n$CH$_3$ or —OCO(CH$_2$)$_n$CF$_3$ (n is an integer of 1 to 4)

<Chemical Formula 4>

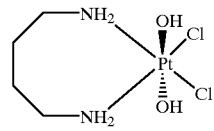

trans, cis-dihydroxo, dichloro-1,4-butanediamine Pt(IV) complex

<Chemical Formula 7>

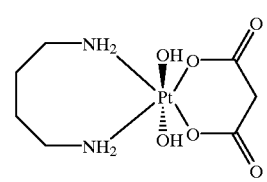

trans-dihydroxo, malonato-1,4-butanediamine Pt(IV) complex.

* * * * *

UNITED STATES PATENT AND TRADEMARK OFFICE
CERTIFICATE OF CORRECTION

PATENT NO. : 6,340,770 B1
DATED : January 22, 2002
INVENTOR(S) : Kwon et al.

It is certified that error appears in the above-identified patent and that said Letters Patent is hereby corrected as shown below:

<u>Title page,</u>
Item [73], Assignee, delete "Sook Myung Women's University" and after "STC NARA CO., LTD.," delete "both".

The correct assignee should read as,
-- [73] Assignee: STC NARA CO., LTD., of Seoul (KR). --

Signed and Sealed this

Eighth Day of October, 2002

Attest:

JAMES E. ROGAN
Attesting Officer     Director of the United States Patent and Trademark Office